US008420567B1

(12) United States Patent
Naumann et al.

(10) Patent No.: US 8,420,567 B1
(45) Date of Patent: Apr. 16, 2013

(54) PROCESS FOR SUPERABSORBENT POLYMER AND CROSSLINKER COMPOSITION

(75) Inventors: Matthias Naumann, Greensboro, NC (US); Stanley A. McIntosh, Greensboro, NC (US); Frank Schubert, Neukirchen-Vluyn (DE); Christoph Loick, Tonisvorst (DE)

(73) Assignee: Evonik Stockhausen, LLC, Greensboro, NC (US)

( * ) Notice: Subject to any disclaimer, the term of this patent is extended or adjusted under 35 U.S.C. 154(b) by 0 days.

(21) Appl. No.: 13/341,132

(22) Filed: Dec. 30, 2011

(51) Int. Cl.
*B01J 20/26* (2006.01)
(52) U.S. Cl.
USPC .......................................... 502/402; 502/401
(58) Field of Classification Search ............... 525/329.5; 502/402
See application file for complete search history.

(56) References Cited

U.S. PATENT DOCUMENTS

| 6,087,450 | A | 7/2000 | Breitbach et al. |
| 6,716,929 | B2 | 4/2004 | Wilson |
| 6,849,665 | B2 * | 2/2005 | Frenz et al. ..................... 521/64 |
| 7,173,086 | B2 | 2/2007 | Smith et al. |
| 7,285,614 | B2 | 10/2007 | Jonas et al. |
| 7,777,093 | B2 | 8/2010 | Smith et al. |
| 7,812,082 | B2 | 10/2010 | McIntosh et al. |
| 8,071,202 | B2 | 12/2011 | Furno et al. |
| 8,247,499 | B2 | 8/2012 | Walden et al. |
| 2008/0234420 | A1 | 9/2008 | Smith et al. |
| 2008/0280128 | A1 | 11/2008 | Furno et al. |
| 2009/0105389 | A1 | 4/2009 | Walden et al. |
| 2009/0227741 | A1 | 9/2009 | Walden et al. |
| 2010/0279860 | A1 | 11/2010 | Smith et al. |

FOREIGN PATENT DOCUMENTS

| DE | 102005018924 A1 | 10/2006 |
| EP | 0339461 A1 | 11/1989 |
| WO | 9522356 A1 | 8/1995 |

OTHER PUBLICATIONS

International Search Report mailed on Aug. 22, 2012 in PCT/US2011/068143.
Written Opinion mailed on Aug. 22, 2012 in PCT/US2011/068143.

* cited by examiner

*Primary Examiner* — Colleen Dunn
*Assistant Examiner* — Haytham Soliman
(74) *Attorney, Agent, or Firm* — Smith Moore Leatherwood LLP; Philip P. McCann

(57) ABSTRACT

The present invention further relates to a process to make a superabsorbent polymer comprising the steps of a) preparing a neutralized monomer solution comprising a polymerizable monomer selected from unsaturated acid groups-containing monomers, ethylenically unsaturated carboxylic acid anhydride, salts, or derivatives thereof and a caustic agent selection from an alkali agent, wherein the polymerizable monomer is neutralized to from about 50 mol % to about 85 mol %; b) forming a crosslinker monomer mixture by adding an internal crosslinker composition to the neutralized monomer solution wherein the internal crosslinking composition is the reaction product of a stoichiometric excess of amine with a glycidyl compound, wherein the internal crosslinker composition has a residual amount of glycidyl compounds of less than about 500 ppm based on the mass of the internal crosslinker composition; and c) polymerizing the crosslinker monomer mixture to make a superabsorbent polymer.

38 Claims, 4 Drawing Sheets

US 8,420,567 B1

PROCESS FOR SUPERABSORBENT POLYMER AND CROSSLINKER COMPOSITION

BACKGROUND

The present invention is directed towards a superabsorbent polymer, particulate superabsorbent polymer compositions, methods to make such products and absorbent articles containing such products, and to a process to make a crosslinker composition. Examples of superabsorbent polymer may include a crosslinked partially neutralized polymer, including crosslinked polyacrylic acids or crosslinked starch-acrylic acid graft polymers, that are capable of absorbing large amounts of aqueous liquids and body fluids, such as urine or blood, with swelling and the formation of hydrogels, and of retaining the aqueous liquids under a certain pressure in accordance with the general definition of superabsorbent polymer. Superabsorbent polymer may be formed into particles, generally referred to as particulate superabsorbent polymer, wherein the particulate superabsorbent polymer may be post-treated with surface crosslinking, surface treatment, and other treatment to form particulate superabsorbent polymer compositions. The acronym SAP may be used in place of superabsorbent polymer, superabsorbent polymer composition, and particles hereof. A primary use of superabsorbent polymer and superabsorbent polymer compositions is in sanitary articles, such as babies' diapers, incontinence products, or sanitary towels. A comprehensive survey of superabsorbent polymers, and their use and manufacture, is given in F. L. Buchholz and A. T. Graham (editors) in "Modern Superabsorbent Polymer Technology," Wiley-VCR, New York, 1998.

Superabsorbent polymers may be prepared by initially neutralizing unsaturated carboxylic acids or derivatives thereof, such as acrylic acid, alkali metal (e.g., sodium and/or potassium) or ammonium salts of acrylic acid, alkyl acrylates, and the like in the presence of a caustic treatment, such as sodium hydroxide, and then polymerizing the product with a relatively small amount of an internal, or monomer, crosslinker such as a di- or poly-functional monomer. The di- or poly-functional monomer materials may serve as covalent internal crosslinking agents to lightly crosslink the polymer chains, thereby rendering them water-insoluble, yet water-swellable. These lightly crosslinked superabsorbent polymers contain a multiplicity of carboxyl groups attached to the polymer backbone. These carboxyl groups generate an osmotic driving force for the absorption of body fluids by the crosslinked polymer network.

In addition to covalent internal crosslinking agents, ionic internal crosslinking agents have been utilized to prepare superabsorbent polymers. The ionic internal crosslinking agents are generally coordination compounds comprising polyvalent metal cations, such as $Al^{3+}$ and $Ca^{2+}$, as disclosed in U.S. Pat. No. 6,716,929 and U.S. Pat. No. 7,285,614. The superabsorbent polymers disclosed in these patents have a slow rate of absorption, due to the presence of ionic crosslinks. In this context, the absorption rate may be measured by a Vortex Test.

Superabsorbent polymers, useful as absorbents in absorbent articles such as disposable diapers, need to have adequately high absorption capacity, as well as adequately high gel strength. Absorption capacity needs to be sufficiently high to enable the absorbent polymer to absorb significant amounts of the aqueous body fluids encountered during use of the absorbent article. Gel strength relates to the tendency of the swollen polymer particles to resist deformation under an applied stress, and needs to be such that the particles do not deform under pressure, and fill the capillary void spaces in the absorbent member, or article, to an unacceptable degree, which is generally called "gel blocking", thereby inhibiting the rate of fluid uptake, or the fluid distribution, by the member or article. Once gel-blocking occurs, it can substantially impede the distribution of fluids to relatively dry zones or regions in the absorbent article, and leakage from the absorbent article can take place well before the particles of absorbent polymer in the absorbent article are fully saturated, or before the fluid can diffuse or wick past the "blocking" particles into the rest of the absorbent article.

U.S. Pat. No. 6,087,450 is directed to providing internal, or monomer, crosslinking agents and superabsorbent polymers cross-linked with them, as well as a process for making the superabsorbent polymer including such internal crosslinking agents. Such internal crosslinking agents are characterized by the fact that by means of reacting, for example, a saturated glycidyl compound with unsaturated amines, for example, allylamines, they open the epoxide ring, thereby forming a hydroxyl group which is optionally available for a subsequent ethoxylation. There are also other reaction paths to produce the cross-linking agents according to the present invention; for example, reacting amines with unsaturated glycidyl compounds, such as (meth)allyl glycidyl ethers or glycidyl (meth) acrylates. However, it has been found that such polymers made in accordance with the technology of the '450 patent may include high residual amounts of the respective glycidyl compounds, which need to be reduced. In particular, it has been found that such polymers may include about 2500 ppm of the respective residual glycidyl compounds. Reduction of the amount of residual glycidyl in the internal crosslinker would make this crosslinker more suitable for the manufacture of polymers such as superabsorbent polymers.

Therefore, there is still a need to improve the content of the respective glycidyl compound(s) of the superabsorbent polymers as set forth in the '450 patent by reducing the residual glycidyl compound(s).

SUMMARY

The present invention includes numerous embodiments, of which some are included herein. One embodiment of the present invention is a process to make a superabsorbent polymer comprising the steps of a) preparing a neutralized monomer solution comprising a polymerized monomer wherein the monomer is selected from unsaturated acid groups-containing monomers, ethylenically unsaturated carboxylic acid anhydride, salts, or derivatives thereof and a caustic agent selection from an alkali agent, wherein the monomer is neutralized to from about 50 mol % to about 85 mol %; b) forming a crosslinker containing monomer mixture by adding an internal crosslinker composition to the neutralized monomer solution wherein the internal crosslinking composition is the reaction product of amine and glycidyl compounds selected from,
(i) saturated amines and/or saturated polyamines with ethylenically unsaturated glycidyl compounds and/or ethylenically unsaturated polyglycidyl compounds, or
(ii) ethylenically unsaturated amines and/or ethylenically unsaturated polyamines with saturated glycidyl compounds and/or saturated polyglycidyl compounds, or
(iii) ethylenically unsaturated amines and/or ethylenically unsaturated polyamines with ethylenically unsaturated glycidyl compounds and/or ethylenically unsaturated polyglycidyl compounds;
wherein the amount of the amines and glycidyl compounds includes a stoichiometric excess of amines/unreacted amino functions, and the internal crosslinker composition has a residual amount of glycidyl compounds of less than about 500 ppm, or less than about 100 ppm, or less than about 5 ppm based on the mass of the internal crosslinker composition as determined by the Glycidyl Compound in Amine-Glycidyl Compound Reaction Products Test set forth herein; and c) polymerizing the crosslinker containing monomer mixture to make a superabsorbent polymer.

Another embodiment of the present invention is directed to a particulate superabsorbent polymer composition having increased permeability wherein the particulate superabsorbent polymer comprises
a) a polymerizable monomer wherein the monomer is selected from unsaturated acid groups-containing monomers, ethylenically unsaturated carboxylic acid anhydride, salts, or derivatives thereof;
b) an internal crosslinker composition that is the reaction product selected from
 (i) saturated amines and/or saturated polyamines with ethylenically unsaturated glycidyl compounds and/or ethylenically unsaturated polyglycidyl compounds, or
 (ii) ethylenically unsaturated amines and/or ethylenically unsaturated polyamines with saturated glycidyl compounds and/or saturated polyglycidyl compounds, or
 (iii) ethylenically unsaturated amines and/or ethylenically unsaturated polyamines with ethylenically unsaturated glycidyl compounds and/or ethylenically unsaturated polyglycidyl compounds;
 wherein components a) and b) are polymerized and granulated to form particulate superabsorbent polymer which has a particle surface, wherein at least 40 wt % of the particulate superabsorbent polymer has a particle size from about 300 µm to about 600 µm;
c) from about 0.01 to about 5 wt % based on the dry particulate superabsorbent polymer composition weight of surface crosslinking agent applied to the particle surface;
wherein the amount of the amines and glycidyl compounds includes a stoichiometric excess of amines/unreacted amino functions, and the internal crosslinker composition has a residual amount of glycidyl compounds of less than about 500 ppm, or less than about 100 ppm, or less than about 5 ppm based on the mass of the internal crosslinker composition as determined by the Glycidyl Compound in Amine-Glycidyl Compound Reaction Products Test set forth herein; and wherein the particulate superabsorbent polymer composition has a Centrifuge Retention Capacity of from 20 g/g to 40 g/g as determined by the Centrifuge Retention Capacity Test set forth herein, and a gel bed permeability of at least about 5 Darcy as determined by the Gel Bed Permeability Test set forth herein.

Another embodiment of the present invention is directed to a process to make a crosslinking composition comprising the step of
preparing a crosslinker monomer mixture by adding an internal crosslinker composition to the neutralized monomer solution wherein the internal crosslinking composition is the reaction product of amines and glycidyl compounds selected from,
 (i) saturated amines and/or saturated polyamines with ethylenically unsaturated glycidyl compounds and/or ethylenically unsaturated polyglycidyl compounds, or
 (ii) ethylenically unsaturated amines and/or ethylenically unsaturated polyamines with saturated glycidyl compounds and/or saturated polyglycidyl compounds, or
 (iii) ethylenically unsaturated amines and/or ethylenically unsaturated polyamines with ethylenically unsaturated glycidyl compounds and/or ethylenically unsaturated polyglycidyl compounds;
wherein the amount of the amines and glycidyl compounds includes a stoichiometric excess of amines/unreacted amino functions.

Numerous other aspects of embodiments, features, and advantages of the present invention will appear from the following detailed description, accompanying drawings, and claims. In the interest of brevity and conciseness, any ranges of values set forth in this specification contemplate all values within the range and are to be construed as support for claims reciting any sub-ranges having endpoints which are real number values within the specified range in question.

These and other aspects, advantages, and salient features of the present invention will become apparent from the following detailed description, the accompanying drawings, and the appended claims.

BRIEF DESCRIPTION OF THE FIGURES

The foregoing and other features, aspects, and advantages of the present invention will become better understood with regard to the following description, appended claims, and accompanying drawings where:

DEFINITIONS

Figure 1:
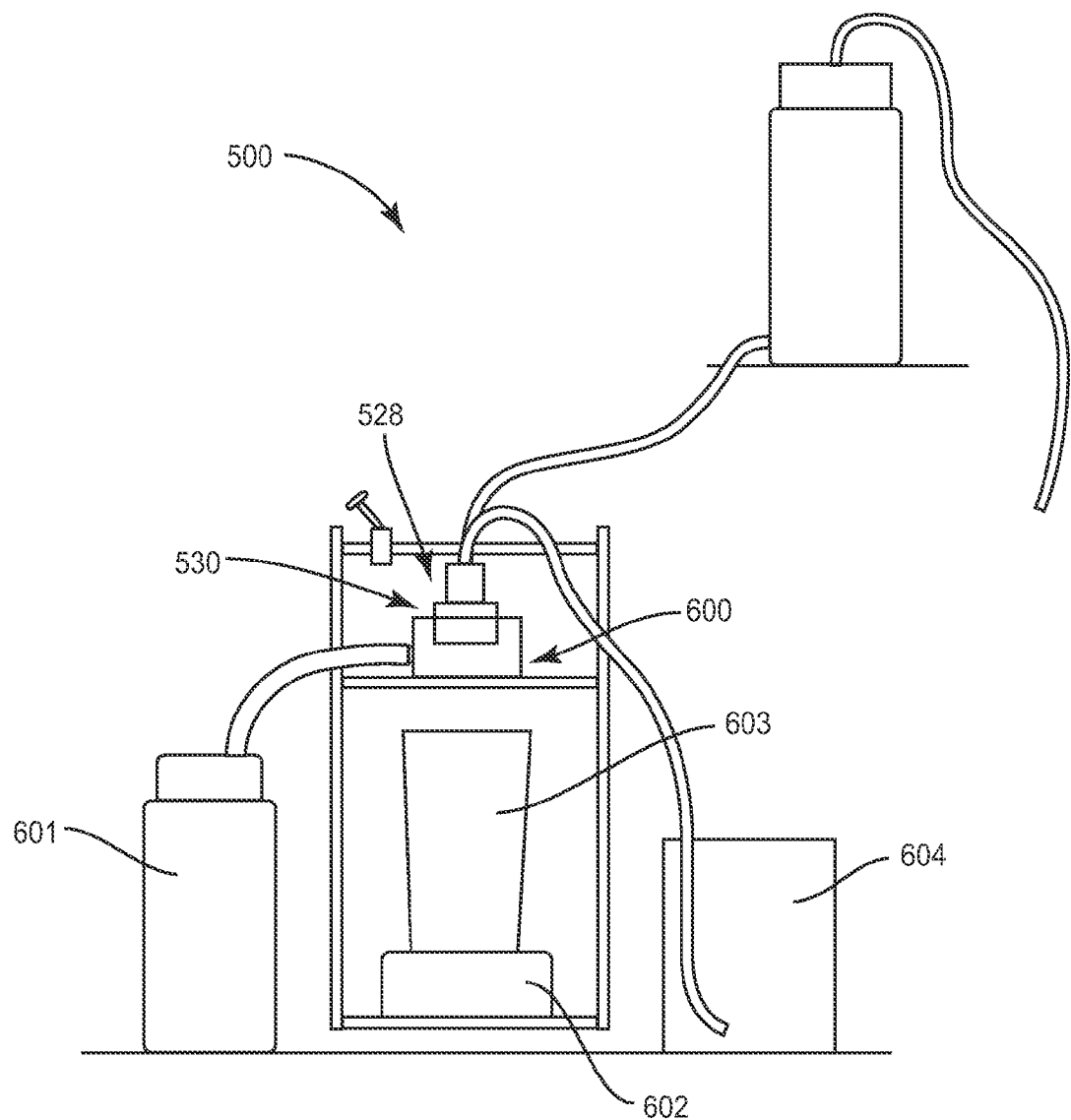
FIG. 1 is a side view of the test apparatus employed for the Free Swell Gel Bed Permeability Test.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about" the claims include equivalents to the quantities.

The term "absorbent article" as used herein refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. Absorbent articles may further include floor cleaning articles, food industry articles, and the like.

The term "Centrifuge Retention Capacity (CRC)" as used herein refers to the ability of the particulate superabsorbent polymer to retain liquid therein after being saturated and subjected to centrifugation under controlled conditions and is stated as grams of liquid retained per gram weight of the sample (g/g) as measured by the Centrifuge Retention Capacity Test set forth herein.

The terms "crosslinked", "crosslink", "crosslinker", or "crosslinking" as used herein refers to any means for effectively rendering normally water-soluble materials substantially water-insoluble but swellable. Such a crosslinking means can include, for example, physical entanglement, crystalline domains, covalent bonds, ionic complexes and associations, hydrophilic associations such as hydrogen bonding, hydrophobic associations, or Van der Waals forces.

The term "internal crosslinker" or "monomer crosslinker" as used herein refers to use of a crosslinker in the monomer solution to form the polymer.

The term "Darcy" as used herein refers to a CGS unit of permeability. One Darcy is the permeability of a solid through which one cubic centimeter of fluid, having a viscosity of one centipoise, will flow in one second through a section one centimeter thick and one square centimeter in cross-section, if the pressure difference between the two sides of the solid is one atmosphere. It turns out that permeability has the same units as area; since there is no SI unit of permeability, square meters are used. One Darcy is equal to about $0.98692 \times 10^{-12}$ $m^2$ or about $0.98692 \times 10^{-8}$ $cm^2$.

The term "diaper" as used herein refers to an absorbent article generally worn by infants and incontinent persons about the lower torso so as to encircle the waist and legs of the wearer and that is specifically adapted to receive and contain urinary and fecal waste.

The term "dry particulate superabsorbent polymer composition" as used herein generally refers to the superabsorbent polymer composition having less than about 10% moisture.

The term "gel permeability" as used herein refers to a property of the mass of particles as a whole and is related to particle size distribution, particle shape, and the connectedness of the open pores between the particles, shear modulus, and surface modification of the swollen gel. In practical terms, the gel permeability of the superabsorbent polymer composition is a measure of how rapidly liquid flows through the mass of swollen particles. Low gel permeability indicates that liquid cannot flow readily through the superabsorbent polymer composition, which is generally referred to as gel blocking, and that any forced flow of liquid (such as a second application of urine during use of the diaper) must take an alternate path (e.g., diaper leakage).

The term "mass median particle size" of a given sample of particles of superabsorbent polymer composition is defined as the particle size, which divides the sample in half on a mass basis, i.e., half of the sample by weight has a particle size greater than the mass median particle size, and half of the sample by mass has a particle size less than the mass median particle size. Thus, for example, the mass median particle size of a sample of superabsorbent polymer composition particles is 2 microns if one-half of the sample by weight is measured as more than 2 microns.

The terms "particle," "particulate," and the like, when used with the term "superabsorbent polymer," refers to the form of discrete units. The units can comprise flakes, fibers, agglomerates, granules, powders, spheres, pulverized materials, or the like, as well as combinations thereof. The particles can have any desired shape: for example, cubic, rod-like polyhedral, spherical or semi-spherical, rounded or semi-rounded, angular, irregular, et cetera.

The terms "particulate superabsorbent polymer" and "particulate superabsorbent polymer composition" refer to the form of superabsorbent polymer and superabsorbent polymer compositions in discrete form, wherein the "particulate superabsorbent polymer" and "particulate superabsorbent polymer compositions" may have a particle size of less than 1000 µm, or from about 150 µm to about 850 µm.

The term "permeability" as used herein refers a measure of the effective connectedness of a porous structure, in this case, crosslinked polymers, and may be specified in terms of the void fraction, and extent of connectedness of the particulate superabsorbent polymer composition.

The term "polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to isotactic, syndiotactic, and atactic symmetries.

The term "polyolefin" as used herein generally includes, but is not limited to, materials such as polyethylene, polypropylene, polyisobutylene, polystyrene, ethylene vinyl acetate copolymer, and the like, the homopolymers, copolymers, terpolymers, etc., thereof, and blends and modifications thereof. The term "polyolefin" shall include all possible structures thereof, which include, but are not limited to, isotatic, synodiotactic, and random symmetries. Copolymers include atactic and block copolymers.

The term "stoichiometric" as used herein refers to the quantitative relationships among substances as they participate in the reaction producing the adduct of the amines and glycidyl compounds.

The term "stoichiometric excess" or "stoichiometric excess of amines" or "stoichiometric excess of amines/unreacted amino functions" as used herein refers to the relation of the amount of the N—H functional groups and the glycidyl compound molecules wherein there are more N—H functional groups than the glycidyl compound molecules in a reaction.

The term "superabsorbent polymer" as used herein refers to water-swellable, water-insoluble organic or inorganic materials including superabsorbent polymers and superabsorbent polymer compositions capable, under the most favorable conditions, of absorbing at least about 10 times their weight, or at least about 15 times their weight, or at least about 25 times their weight in an aqueous solution containing 0.9 weight percent sodium chloride.

The term "superabsorbent polymer composition" as used herein refers to a superabsorbent polymer comprising a surface additive in accordance with the present invention.

The term "surface crosslinking" as used herein refers to the level of functional crosslinks in the vicinity of the surface of the superabsorbent polymer particle, which is generally higher than the level of functional crosslinks in the interior of the superabsorbent polymer particle. As used herein, "surface" describes the outer-facing boundaries of the particle.

The term "thermoplastic" as used herein describes a material that softens when exposed to heat and which substantially returns to a non-softened condition when cooled to room temperature.

The term "% by weight" or "% wt" as used herein and referring to components of the dry particulate superabsorbent polymer composition, is to be interpreted as based on the weight of the dry superabsorbent polymer composition, unless otherwise specified herein.

These terms may be defined with additional language in the remaining portions of the specification.

DETAILED DESCRIPTION

While typical aspects of embodiment and/or embodiments have been set forth for the purpose of illustration, this Detailed Description and the accompanying drawings should not be deemed to be a limitation on the scope of the invention. Accordingly, various modifications, adaptations, and alternatives may occur to one skilled in the art without departing from the spirit and scope of the present invention. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

It is the object of the present invention to provide a process to make a superabsorbent polymer and a particulate superabsorbent polymer composition cross-linked with at least one internal crosslinker composition, as well as and the superabsorber polymers are suitable for use in diaper constructions or other technical applications, as well as a process to make the crosslinker composition.

One embodiment of the present invention is a process to make a superabsorbent polymer comprising the steps of a) preparing a neutralized monomer solution comprising a polymerized monomer wherein the monomer is selected from unsaturated acid groups-containing monomers, ethylenically unsaturated carboxylic acid anhydride, salts, or derivatives thereof and a caustic agent selection from an alkali agent, wherein the monomer is neutralized to from about 50 mol % to about 85 mol %; b) forming a monomer mixture by adding an internal crosslinker composition to the neutralized monomer solution wherein the internal crosslinking composition is the reaction product of amine and glycidyl compounds selected from, (i) saturated amines and/or saturated polyamines with ethylenically unsaturated glycidyl compounds and/or ethylenically unsaturated polyglycidyl compounds, or (ii) ethylenically unsaturated amines and/or ethylenically unsaturated polyamines with saturated glycidyl compounds and/or saturated polyglycidyl compounds, or (iii) ethylenically unsaturated amines and/or ethylenically unsaturated polyamines with ethylenically unsaturated glycidyl compounds and/or ethylenically unsaturated polyglycidyl compounds;

wherein the amount of the amines and glycidyl compounds includes a stoichiometric excess of amines, and the internal crosslinker composition has a residual glycidyl of less than about 500 ppm as determined by the Glycidyl Compound in Amine-Glycidyl Compound Reaction Products Test set forth herein; and c) polymerizing the monomer mixture to make a superabsorbent polymer.

Another embodiment of the present invention is directed to a particulate superabsorbent polymer composition having increased permeability wherein the particulate superabsorbent polymer comprises a) a polymerizable monomer wherein the monomer is selected from unsaturated acid groups-containing monomers, ethylenically unsaturated carboxylic acid anhydride, salts, or derivatives thereof;

b) an internal crosslinker composition that is the reaction product selected from (i) saturated amines and/or saturated polyamines with ethylenically unsaturated glycidyl compounds and/or ethylenically unsaturated polyglycidyl compounds, or (ii) ethylenically unsaturated amines and/or ethylenically unsaturated polyamines with saturated glycidyl compounds and/or saturated polyglycidyl compounds, or (iii) ethylenically unsaturated amines and/or ethylenically unsaturated polyamines with ethylenically unsaturated glycidyl compounds and/or ethylenically unsaturated polyglycidyl compounds;

wherein components a) and b) are polymerized and granulated to form particulate superabsorbent polymer which has a particle surface, wherein at least 40 wt % of the particulate superabsorbent polymer has a particle size from about 300 µm to about 600 µm;

c) from about 0.01 to about 5 wt % based on the dry particulate superabsorbent polymer composition weight of surface crosslinking agent applied to the particle surface;

wherein the amount of the amines and glycidyl compounds includes a stoichiometric excess of amines, and the internal crosslinker composition has a residual amount of glycidyl compounds of less than about 500 ppm as determined by the Glycidyl Compound in Amine-Glycidyl Compound Reaction Products Test set forth herein; and wherein the particulate superabsorbent polymer composition has a Centrifuge Retention Capacity of from about 20 g/g to about 40 g/g, and a gel bed permeability of at least about 5 Darcy, and an Absorption at Pressure at 0.7 psi (AAP(0.7 psi)) from about 15 g/g to about 30 g/g, and a Saline Flow Conductivity (SFC) from about $20 \times 10^{-7}$ cm sec/g to about $200 \times 10^{-7}$ cm sec/g.

Another embodiment of the present invention is directed to a process to make a crosslinking composition comprising the step of a) preparing a crosslinker monomer mixture by adding an internal crosslinker composition to the neutralized monomer solution wherein the internal crosslinking composition is the reaction product of amines and glycidyl compounds selected from, (i) saturated amines and/or saturated polyamines with ethylenically unsaturated glycidyl compounds and/or ethylenically unsaturated polyglycidyl compounds, or (ii) ethylenically unsaturated amines and/or ethylenically unsaturated polyamines with saturated glycidyl compounds and/or saturated polyglycidyl compounds, or (iii) ethylenically unsaturated amines and/or ethylenically unsaturated polyamines with ethylenically unsaturated glycidyl compounds and/or ethylenically unsaturated polyglycidyl compounds;

wherein the stoichiometric amount of the amines and glycidyl compounds includes a stoichiometric excess of amines.

The process to make a superabsorbent polymer as set forth in embodiments of the present invention is obtained by the initial polymerization of from about 55% to about 99.9% by weight of the superabsorbent polymer of polymerizable unsaturated acid group containing monomer. A suitable polymerizable monomer includes any of those containing carboxyl groups, such as acrylic acid, methacrylic acid, or 2-acrylamido-2-methylpropanesulfonic acid, or mixtures thereof. It is desirable for at least about 50% by weight, and more desirable for at least about 75% by weight of the acid groups to be carboxyl groups.

As to acrylic acid, it is important to use acrylic acid that is known by its contents to be pure, that is the acrylic acid having at least 99.5 wt % concentration, or at least 99.7 wt % concentration, or at least 99.8% concentration. The principal component of this monomer may be either acrylic acid, or acrylic acid and an acrylate salt. Impurities in acrylic acid may include water, propionic acid, acetic acid, and diacrylic acid, commonly called acrylic acid dimer. Content of the diacrylic acid should be 1000 ppm or less, or 500 ppm or less, or 300 ppm or less, when the acrylic acid is used in the process. In addition, it is important to minimize the generation of β-hydroxyproprionic acid during the neutralization process to less than about 1000 ppm, or less than about 500 ppm, of β-hydroxyproprionic acid.

Moreover, in the acrylic acid, the content of protoanemonin and/or furfural is 0 to 20 ppm by weight in terms of the converted value based on acrylic acid. In the light of improvement physical properties and characteristics of the water absorbing resin, content of protoanemonin and/or furfural in the monomer is not higher than 10 ppm by weight, or from 0.01 to 5 ppm by weight, or from 0.05 to 2 ppm by weight, or from 0.1 to 1 ppm by weight in terms of the converted value based on acrylic acid.

Further, in the monomer, it is preferred that the amount of aldehyde component other than furfural and/or maleic acid is as small as possible for the same reason. Specifically, the content of the aldehyde component other than furfural and/or maleic acid may be from 0 to 5 ppm by weight, or from 0 to about 3 ppm by weight, or from 0 to about 1 ppm by weight, or 0 ppm by weight (not higher than detection limit) in terms of the converted value based on acrylic acid. Examples of the aldehyde component other than furfural include benzaldehyde, acrolein, acetaldehyde and the like.

Additionally, in the monomer or particulate superabsorbent polymer of the present invention, content of saturated carboxylic acid consisting of acetic acid and/or propionic acid, not higher than about 1000 ppm by weight, or from about 10 to about 800 ppm by weight, or from about 100 to about 500 ppm by weight in terms of the converted value based on acrylic acid.

In some aspects, the suitable monomer that can be copolymerized with the ethylenically unsaturated monomer may include, but is not limited to, acrylamide, methacrylamide, hydroxyethyl acrylate, dimethylaminoalkyl (meth)-acrylate, ethoxylated (meth)-acrylates, dimethylaminopropylacrylamide, or acrylamidopropyltrimethylammonium chloride. Such monomer may be present in a range of from 0% to about 50 wt % based on the acrylic acid of the copolymerized monomer.

The acid groups are neutralized to the extent of at least about 25 mol %, that is, the acid groups are desirably present as sodium, potassium, or ammonium salts. The neutralization may be accomplished by either adding a caustic solution to a monomer solution, or by adding the monomer solution to a caustic solution. In some aspects, the degree of neutralization may be at least about 50 mol % or may be from about 50 mol % to about 85 mol %. In some aspects, it is desirable to utilize polymers obtained by polymerization of acrylic acid or methacrylic acid, the carboxyl groups of which are neutralized to the extent of from about 50 mol % to about 80 mol %, in the presence of internal crosslinking agents.

When partially neutralized or completely neutralized acrylate salt is turned into the polymer in the particulate water absorbing agent following polymerization, the converted value based on acrylic acid may be determined through converting the partially neutralized or completely neutralized polyacrylate salt is assumed to be entirely the equimolar unneutralized polyacrylic acid.

For convenience the term amines as used herein shall collectively and individually refer to saturated amines, saturated polyamines, ethylenically unsaturated amines and/or ethylenically unsaturated polyamines; and the term glycidyl compounds as used herein shall collectively and individually refer to ethylenically unsaturated glycidyl compounds, ethylenically unsaturated polyglycidyl compounds, saturated glycidyl compounds, and/or saturated polyglycidyl compounds The superabsorbent polymer includes crosslinking points wherein the superabsorbent polymer can be crosslinked with an internal crosslinking composition. Suitable internal crosslinker compositions in this embodiment may include, but are not limited to an internal crosslinker composition which is the reaction product of amine and glycidyl compounds selected from,
  (i) saturated amines and/or saturated polyamines with ethylenically unsaturated glycidyl compounds and/or ethylenically unsaturated polyglycidyl compounds, or
  (ii) ethylenically unsaturated amines and/or ethylenically unsaturated polyamines with saturated glycidyl compounds and/or saturated polyglycidyl compounds, or
  (iii) ethylenically unsaturated amines and/or ethylenically unsaturated polyamines with ethylenically unsaturated glycidyl compounds and/or ethylenically unsaturated polyglycidyl compounds
wherein the reaction amount of the amines and glycidyl compounds includes a stoichiometric excess of amines. In particular, the amount of the glycidyl groups may be from about 75 wt % to about 99 wt % of the molar amount of NH-functions, or from about 85 wt % to about 98 wt %, or from about 90 wt % to about 97 wt % of the molar amount of NH-functions.

This object is achieved by using internal crosslinking compositions, which are characterized by means of reacting a glycidyl compound with amines or polyamines, for example, allylamines or alkylenediamines, they open the epoxide ring, thereby forming a hydroxyl group which is optionally available for a subsequent ethoxylation. The hydroxyl group can be ethoxylated when a catalyst such as NaOH or KOH is used.

The internal crosslinker compositions as set forth above have an excess stoichiometric amount of the amines/NH-functions that can be taken care of by reacting the amines/NH-functions with an alkylene oxide, such as EO or PO, and remove the excess of the non-rected alkylene oxide by the application of a slight vacuum. The internal crosslinker composition has a residual amount of glycidyl compounds of less than about 500 ppm, or less than about 100 ppm or less than about 5 ppm based on the mass of the internal crosslinker composition as determined by the Glycidyl Compound in Amine-Glycidyl Compound Reaction Products Test set forth herein.

The internal crosslinker compositions set forth above may be prepare by a process comprising the step of
a) preparing a crosslinker monomer mixture by reacting amines and glycidyl compounds selected from,
  (i) saturated amines and/or saturated polyamines with ethylenically unsaturated glycidyl compounds and/or ethylenically unsaturated polyglycidyl compounds, or
  (ii) ethylenically unsaturated amines and/or ethylenically unsaturated polyamines with saturated glycidyl compounds and/or saturated polyglycidyl compounds, or
  (iii) ethylenically unsaturated amines and/or ethylenically unsaturated polyamines with ethylenically unsaturated glycidyl and/or ethylenically unsaturated polyglycidyl compounds;
wherein the amount of the amines and glycidyl compounds includes a stoichiometric excess of amines, and the internal crosslinker composition has a residual amount of glycidyl compounds of less than about 500 ppm, or less than about 100 ppm, or less than about 5 ppm based on the mass of the internal crosslinker composition as determined by the Glycidyl Compound in Amine-Glycidyl Compound Reaction Products Test set forth herein.

In particular, the foregoing internal crosslinking composition may be prepared by:

a) prepare a reaction vessel equipped with an agitator, heating and cooling facilities and a vacuum system purged with nitrogen;

b) add the amine and water to the vessel of a) and heating the additives to from about 70 to about 90° C.;

c) adding the glycidyl composition at the raised temperature to the additives in the vessel under agitation and cooling, wherein the amount of the amines and glycidyl compounds includes a stoichiometric excess of amines;

d) heat the mixture to from about 100° C. to about 120° C.;

e) remove the water from the mixture by distillation; and f) remove the final product.

The crosslinking agents of the present invention may be alkoxylated at the site of the free hydroxyl or NH groups. Without being limited by the following, it is known that the free NH groups are much more reactive than the free hydroxyl groups, which usually require a catalyst such as NaOH or KOH for the reaction. To this end, the alcohols according to the present invention may be reacted, for example, with ethylene or propylene oxide, or their mixtures. The alcohols may be reacted with ethylene oxide(EO) or propylene oxide(PO). This may also result in an improved water solubility of the cross-linker. Up to 45 moles EO, or up to 20 moles EO, or up to 12 moles EO may be added per hydroxyl group. This will also work for residual NH groups. NH-groups are even more reactive and can be reacted without alkaline or acidic catalysts. The understoichiometric amounts of glycidyl compounds with respect to NH-functions will leave some unreacted NH-functions at the end of the reaction and helps to reduce the residual amounts of glycidyl compounds to the desired limits of less than 500 ppm, or less than 50 ppm or less than 5 ppm as determined by the Allyl Glycidyl Ether (AGE) in Amine-AGE Reaction Products Test. In addition, the above-mentioned polyethylene glycol chains of the glycidyl compounds may comprise up to 45, or up to 20, or up to 12 ethylene glycol units. In case of the use of PO without any additional catalyst, the residual amounts of NH-functions may be directly propoxylated, forming secondary alcohol groups. The excess of PO is easily removed by applying a slight vacuum.

There are also other reaction paths to produce the cross-linking agents according to the present invention; for example, reacting amines with unsaturated glycidyl compounds, such as (meth)allyl glycidyl ethers or glycidyl (meth) acrylates. In accordance with the different reaction possibilities of producing these cross-linker structures, various crosslinker compositions may be derived and are set forth herein.

In particular, the internal crosslinker may be made by preparing a solution of an amine and water being charged into a reactor including an agitator, heating and cooling facilities. The solution is heated from about 60 to about 100° C. A selected amount of the glycidyl compound is added over a time period under agitation and cooling. The reaction mixture is heated, and water is distilled off under vacuum and the final product is cooled to room temperature. More specific details about making the internal crosslinker asset forth herein can be found in the Examples section of this application.

Suitable reaction components to produce the unsaturated amino/glycidyl cross-linking agents according to the present invention, for example, are set out in the following.

The saturated amines, ethylenically unsaturated amines, saturated polyamines, and/or ethylenically unsaturated polyamines may include aliphatic as well as aromatic, heterocyclic and cyclic compounds as suitable amines components for the reaction with the glycidyl compounds; including for example, (mono, di and poly)aminoalkanes, (mono, di and poly)aminopolyethers, allylamine, alkyl(meth)allylamines, e.g., methyl allylamine, methyl methallylamine, ethyl methallylamine, and ethyl allylamine; methyl-, ethyl-, propyl- and butylamine, diallylamine, dimethallylamine, aniline, ethylenediamine, diethylenetriamine, hexamethylenediamine, trimethylhexamethylenediamine, neopentane diamine, 1,2-propylenediamine, 4,7-dioxadecane-1,10-diamine, 4,9-dioxadodecane-1,12-diamine, polyether diamines, polyalkylene glycol diamines, 3-amino-1-methylaminopropane, bis(3-aminopropyl)methylamine, isophorone diamine, 4,4'-diaminodicyclohexylmethane, 1-(2-aminoethyl)piperazine, o-, m-, or p-phenylenediamine, 4,4'-diaminodiphenylmethane, 1,4-diaminoanthraquinone, 2,4,6-triamino-1,3,5-triazine, aminopyridine, glucosamine, and mixtures thereof.

The ethylenically unsaturated glycidyl compounds, ethylenically unsaturated polyglycidyl compounds, saturated glycidyl compounds, and/or saturated polyglycidyl compounds to be used according to the present invention may be mono-, di- or polyfunctional. Examples of monofunctional glycidyl compounds used alone or in admixture include: ethylene glycol monoglycidyl ether and the related $C_1$-$C_6$-alkyl ethers or esters; glycidol, ethylene oxide, propylene oxide, (meth) allyl glycidyl ethers, polyethylene glycol monoglycidyl ethers and the related $C_1$-$C_6$-alkyl ethers or esters; vinyl glycidyl ethers, glycidyl(meth)acrylates, glycidyl(meth)allyl ethers, or 1-halogen-2,3-epoxypropane. Ethylene glycol or polyglycol diglycidyl ethers; glycerol, trimethylolpropane, or pentaerythritol triglycidyl ethers; polyglycerol polyglycidyl ethers, sorbitol polyglycidyl ethers, or their mixtures are used as multifunctional glycidyl ethers.

The following structures as shown in Table 1 may be examples for suitable glycidyl compounds.

TABLE 1

| Name | Structure |
|---|---|
| allyl glycidyl ether (AGE) | 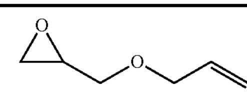 |
| glycidyl methacrylate | 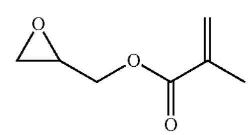 |
| glycidyl acrylate | 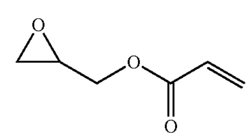 |
| EGDGE (ethylene glycol diglycidylether) | |

Some examples of internal crosslinking agents according to the present invention include, but are not limited to, diallylaminoethanol, diallylaminopolyglycol ether, 1,3-bis(diallylamino)-2-propanol, N,N-diallylamino-1-amino-3-allyloxy-2-propanol, polyethylene glycol di(N,N-diallyl-3-amino-2-hydroxy-prop-1-yl)ether, ethylene glycol di(N,N-diallyl-3-amino-2-hydroxy-prop-1-yl)ether, alkoxylated 1,3-bis(diallylamino)-2-propanol, alkoxylated 1-allyloxy-3-(diallylamino)-2-propanol, alkoxylated polyethylene glycol di(N,N-diallyl-3-amino-2-hydroxy-prop-1-yl)ether, alkoxylated ethylene glycol di(N,N-diallyl-3-amino-2-hydroxy-prop-1-yl)ether, N,N-di(allyloxy-2-hydroxy-prop-3-yl) aniline, alkoxylated N,N-di(allyloxy-2-hydroxy-prop-3-yl) aniline, 1,2-bis[N,N-di(allyloxy-2-hydroxy-prop-3-yl)] ethane and bis[N,N-di(allyloxy-2-hydroxy-prop-3-yl)] aminoethyl-(allyloxy-2-hydroxy-prop-3-yl)amine tetrakis-N,N,N',N'[3-allyloxyhydroxy propyl]ethylene diamine, plus alkoxylated products thereof. The above-mentioned polyethylene glycol ether units may comprise a maximum of 45 moles of ethylene oxide and/or propylene oxide, or a maximum of 20, or a maximum of 15 moles of ethylene oxide and/or propylene oxide. According to another embodiment of the present invention, the N-atoms of the cross-linkers are partially or completely quaternized.

The internal crosslinker compositions, or their mixtures, to be used according to the present invention may be used in amounts in the superabsorbent polymer of from about 0.01 to about 3.0%-wt., or from about 0.05 to about 1.5%-wt., or from about 0.1 to about 1.0%-wt., relative to the monomers.

In another embodiment, the superabsorbent polymer may include from about 0.001 to about 0.1 wt % based on the monomer of a second internal crosslinker which may comprise compositions comprising at least two ethylenically unsaturated double-bonds, for example, methylenebisacrylamide or -methacrylamide or ethylenebisacrylamide; additionally, esters of unsaturated mono- or polycarboxylic acids of polyols, such as, diacrylates or triacrylates, e.g., butanediol- or ethylene glycol diacrylate or -methacrylate; trimethylolpropane triacrylate, as well as their alkoxylated derivatives; additionally, allyl compounds, such as allyl (meth)acrylate, triallyl cyanurate, maleic acid diallyl ester, polyallyl ester, tetraallyloxyethane, di- and triallylamine, tetrallylethylenediamine, allyl esters of phosphoric acid or phosphorous acid. One such example is SR-454 an ethoxylated (3) trimethylolpropance triacrylate commercially available from the Sartomer Company, Exton, Pa. Moreover, compounds having at least one functional group reactive towards acid groups may also be used. Examples thereof include N-methylol compounds of amides, such as methacrylamide or acrylamide, and the ethers derived therefrom, as well as di- and polyglycidyl compounds.

In some aspects, initiators can be used for initiation of the free-radical polymerization. Suitable initiators include, but are not limited to, azo or peroxo compounds, redox systems or ultraviolet initiators, sensitizers, and/or radiation.

After polymerization, the superabsorbent polymer is generally formed into superabsorbent polymer particles, or particulate superabsorbent polymer. While superabsorbent polymer particles may be used by way of example of the physical form of superabsorbent polymer composition, the invention is not limited to this form and is applicable to other forms such as fibers, foams, films, beads, rods, and the like. The particulate superabsorbent polymer of the present invention generally includes particle sizes ranging from about 50 to about 1000 µm, or from about 150 to about 850 µm. The present invention may include at least about 40 wt % of the particles having a particle size from about 300 µm to about 600 µm, at least about 50 wt % of the particles having a particle size from about 300 µm to about 600 µm, or at least about 60 wt % of the particles having a particle size from about 300 µm to about 600 µm as measured by screening through a U.S. standard 30 mesh screen and retained on a U.S. standard 50 mesh screen. In addition, the size distribution of the superabsorbent polymer particles of the present invention may include less than about 30% by weight of particles having a size greater than about 600 µm, and less than about 30% by weight of particles having a size of less than about 300 µm as measured using for example a RO-TAP® Mechanical Sieve Shaker Model B available from W. S. Tyler, Inc., Mentor Ohio.

In one embodiment, the particulate superabsorbent polymer may then be surface treated with additional chemicals and treatments as set forth herein. In particular, the surface of the particulate superabsorbent polymer may be crosslinked, generally referred to as surface crosslinked, by the addition of a surface crosslinking agent and heat-treatment. In general, surface crosslinking is a process that is believed to increase the crosslink density of the polymer matrix in the vicinity of the particulate superabsorbent polymer surface with respect to the crosslinking density of the particle interior.

Desirable surface crosslinking agents may include chemicals with one or more functional groups that are reactive toward pendant groups of the polymer chains, typically the acid groups. Surface crosslinker agents may include compounds that comprise at least two functional groups which can react with functional groups of a polymer structure in a condensation reaction (condensation crosslinker), in an addition reaction or in a ring opening reaction. These compounds may include condensation crosslinkers such as, for example, diethylene glycol, triethylene glycol, polyethylene glycol, glycerine, polyglycerine, propylene glycol, diethanolamine, triethanolamine, polyoxypropylene, oxyethylene-oxypropylene block copolymers, sorbitan fatty acid esters, polyoxyethylene sorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one as well as 1,3-dioxolan-2-one. The amount of the surface crosslinking agent may be present in an amount of from about 0.01% to about 5% by weight of the dry particulate superabsorbent polymer composition weight, and such as from about 0.1% to about 3% by weight, and such as from about 0.1% to about 1% by weight, based on the weight of the dry particulate superabsorbent polymer composition weight.

After the particulate superabsorbent polymer have been brought into contact with the surface crosslinker or with the fluid comprising the surface crosslinker, the treated particulate superabsorbent polymer are heat treated which may include heating the coated particulate superabsorbent polymer to a temperature of from about 50 to about 300° C., or from about 75 to about 275° C., or from about 150 to about 250° C., so that the outer region of the polymer structures is more strongly crosslinked compared to the inner region (i.e., surface crosslinking). The duration of the heat treatment is limited by the risk that the desired property profile of the polymer structures will be destroyed as a result of the effect of heat.

In another embodiment, the fluid comprising the surface crosslinker, may further include other ingredients, separately or together, including multivalent metal cations such as aluminum sulfate or aluminum lactate, and an insoluble, inorganic powder such as a silica including SIPERNAT® 22S fumed silica available from Evonik, which ingredients will be hereafter described in more detail.

In one particular aspect of surface crosslinking, the particulate superabsorbent polymer is coated or surface-treated with an alkylene carbonate followed by heating to affect surface crosslinking, which can improve the surface crosslinking density and the gel strength characteristics of the superabsorbent polymer particle. More specifically, the surface crosslinking agent is coated onto the superabsorbent polymer particulate by mixing the particulate superabsorbent polymer with an aqueous alcoholic solution of the alkylene carbonate surface crosslinking agent. The amount of alcohol in the aqueous alcoholic solution may be determined by the solubility of the alkylene carbonate and is kept as low as possible for various reasons, for instance, for protection against explosions. Suitable alcohols are methanol, isopropanol, ethanol, butanol, or butyl glycol, as well as mixtures of these alcohols. In some aspects, the solvent desirably is water, which typically is used in an amount of about 0.3% by weight to about 5.0% by weight, based on the weight of the dry superabsorbent polymer.

In other aspects, the alkylene carbonate surface crosslinking agent is dissolved in water without any alcohol. In still other aspects, the alkylene carbonate surface crosslinking agent may be applied from a powder mixture, for example, with an inorganic carrier material, such as silicone dioxide ($SiO_2$), or in a vapor state by sublimation of the alkylene carbonate.

To achieve the desired surface crosslinking properties, the alkylene carbonate should be distributed evenly on the particulate superabsorbent polymer. For this purpose, mixing is effected in suitable mixers known in the art, such as fluidized bed mixers, paddle mixers, rotary drum mixers, or twin-worm mixers. It is also possible to carry out the coating of the particulate superabsorbent polymer during one of the process steps in the production of the particulate superabsorbent polymer. In one particular aspect, a suitable process for this purpose is the inverse suspension polymerization process.

The heat treatment, which follows the coating treatment of the particulate superabsorbent polymer, may be carried out as follows. In general, the heat treatment is at a temperature of from about 100° C. to about 300° C. Lower temperatures are possible if highly reactive epoxide crosslinking agents are used. However, if alkylene carbonates are used, then the thermal treatment is suitably at a temperature of from about 150° C. to about 250° C. In this particular aspect, the treatment temperature depends on the dwell time and the kind of alkylene carbonate. For example, at a temperature of about 150° C., the thermal treatment is carried out for one hour or longer. In contrast, at a temperature of about 250° C., a few minutes (e.g., from about 0.5 minutes to about 5 minutes) are sufficient to achieve the desired surface crosslinking properties. The thermal treatment may be carried out in conventional dryers or ovens known in the art.

In addition to surface crosslinking, the particulate superabsorbent polymer compositions may be further surface treated with other chemical compositions. In some aspects, the particulate superabsorbent polymer composition of the present invention may be surface treated with from 0% to about 5 wt %, and from about 0.001% to about 5 wt %, or from about 0.01% to about 0.5 wt % of the dry particulate superabsorbent polymer composition weight of a polymeric coating, such as a thermoplastic coating, or a cationic coating, or a combination of a thermoplastic coating and a cationic coating. In some particular aspects, the polymeric coating desirably is a polymer that may be in a solid, emulsion, suspension, colloidal, or solubilized state, or combinations thereof. Polymeric coatings suitable for this invention may include, but are not limited to, a thermoplastic coating having a thermoplastic melt temperature wherein the polymeric coating is applied to the particle surface coincident with or followed by a temperature of the treated superabsorbent polymer particle at about the thermoplastic melt temperature.

Examples of thermoplastic polymers include polyolefin, polyethylene, polyester, polyamide, polyurethane, styrene polybutadiene, linear low density polyethylene (LLDPE), ethylene acrylic acid copolymer (EAA), ethylene alkyl methacrylate copolymer (EMA), polypropylene (PP), maleated polypropylene, ethylene vinyl acetate copolymer (EVA), polyester, polyamide, and blends of all families of polyolefins, such as blends of PP, EVA, EMA, EEA, EBA, HDPE, MDPE, LDPE, LLDPE, and/or VLDPE, may also be advantageously employed. The term polyolefin as used herein is defined above. In particular aspects, maleated polypropylene is a preferred thermoplastic polymer for use in the present invention. A thermoplastic polymer may be functionalized to have additional benefits such as water solubility or dispersability.

Polymeric coatings of this invention may also include a cationic polymer. A cationic polymer as used herein refers to a polymer or mixture of polymers comprising a functional group or groups having a potential of becoming positively charged ions upon ionization in an aqueous solution. Suitable functional groups for a cationic polymer include, but are not limited to, primary, secondary, or tertiary amino groups, imino groups, imido groups, amido groups, and quaternary ammonium groups. Examples of synthetic cationic polymers include the salts or partial salts of poly(vinyl amines), poly (allylamines), poly(ethylene imine), poly(amino propanol vinyl ethers), poly(acrylamidopropyl trimethyl ammonium chloride), poly(diallyldimethyl ammonium chloride). Examples of natural-based cationic polymers include partially deacetylated chitin, chitosan, and chitosan salts. Synthetic polypeptides such as polyasparagins, polylysines, polyglutamines, and polyarginines are also suitable cationic polymers.

The absorbent polymers according to the invention can include from 0 to about 5 wt % of a penetration modifier that is added immediately before, during or immediately after the surface crosslinking. Examples of penetration modifiers include compounds which alter the penetration depth of surface-modifying agents into the superabsorbent polymer particle, fiber, film, foam or bead by changing the viscosity, surface tension, ionic character or adhesion of said agents or medium in which these agents are applied. Preferred penetration modifiers are, polyethylene glycols, tetraethylene glycol dimethyl ether, monovalent metal salts, surfactants and water soluble polymers.

The absorbent polymers according to the invention can include from 0 to about 5 wt %, or from about 0.01 wt % to about 1 wt %, or from about 0.01 wt % to about 0.5 wt % based on the dry particulate superabsorbent polymer composition weight, of a multivalent metal salt, based on the weight of the mixture, on the surface of the polymer. The multivalent metal salt is preferably water soluble. Examples of preferred metal cations include the cations of Al, Fe, Zr, Mg, Ce, and Zn. Preferably, the metal cation has a valence of at least +3, with Al being most preferred. Examples of preferred anions in the multivalent metal salt include halides, chlorohydrates, sulfates, nitrates, lactates, and acetates, with chlorides, sulfates, lactates, and acetates being preferred, sulfates and lactates being more preferred. Aluminum sulfate is the most preferred multivalent metal salt and is readily commercially available. The preferred form of aluminum sulfate is hydrated aluminum sulfate, preferably aluminum sulfate having from 12 to 14 waters of hydration. Mixtures of multivalent metal salts may also be employed.

The polymer and multivalent metal salt suitably are mixed by dry blending, or preferably in solution, using means well known to those skilled in the art. Aqueous solutions are preferred. With dry blending, a binder may be employed in an amount which sufficient to ensure that a substantially uniform mixture of the salt and the superabsorbent polymer is maintained. The binder may be water or a nonvolatile organic compound having a boiling point of at least 150° C. Examples of binders include water, polyols such as propylene glycol, glycerin and poly(ethylene glycol).

The absorbent polymers according to the invention can comprise include from about 0.01 to about 5 wt % based on the dry particulate superabsorbent polymer composition weight of water-insoluble, inorganic powder. Examples of insoluble, inorganic powders include silicon dioxide, silicic acid, silicates, titanium dioxide, aluminum oxide, magnesium oxide, zinc oxide, talc, calcium phosphate, clays, diatomataceous earth, zeolites, bentonite, kaolin, hydrotalcite, activated clays, etc. One example of water-insoluble, inorganic powder includes SIPERNAT® 22S silica, which is available from Evonik Industries. The insoluble inorganic powder additive may be a single compound or a mixture of compounds selected from the above list. Of all these examples, amorphous silicon dioxide or aluminum oxide preferred. Further, a particle diameter of the inorganic powder may be 1,000 μm or smaller, or 100 μm or smaller.

The superabsorbent polymer according to the invention may also include the addition of from 0 to about 5 wt % based on the dry particulate superabsorbent polymer composition weight of a surfactant to the polymer particle surface. The water-insoluble, inorganic powder may be added immediately prior to, during or immediately after the surface crosslinking step.

In some aspects, the particulate superabsorbent polymer compositions according to the invention may include from 0 wt % to about 5 wt %, or from about 0.01 wt % to about 3 wt % of the dry particulate superabsorbent polymer composition of silica. Examples of silica include fumed silica, precipitated silica, silicon dioxide, silicic acid, and silicates. In some particular aspects, microscopic noncrystalline silicon dioxide is desirable. In some aspects, the particle diameter of the inorganic powder can be 1,000 mm or smaller, such as 100 μm or smaller.

In some aspects, the particulate superabsorbent polymer compositions may also include from 0% to about 30 wt % of the dry superabsorbent polymer composition, such as from about 0.1% to about 5 wt %, of water-soluble polymers based by weight of the dry particulate superabsorbent polymer composition weight, such as partly or completely hydrolyzed polyvinyl acetate, polyvinylpyrrolidone, starch or starch derivatives, polyglycols, polyethylene oxides, polypropylene oxides, or polyacrylic acids. In some particular aspects, the water-soluble polymers are desirably in polymerized-in form.

In some aspects, additional surface additives may optionally be employed with the particulate superabsorbent polymer compositions, including odor-binding substances, such as cyclodextrins, zeolites, inorganic or organic salts, and similar materials; anti-caking additives, flow modification agents, surfactants, viscosity modifiers, and the like. In addition, surface additives may be employed that perform several roles during surface modifications. For example, a single additive may be a surfactant, viscosity modifier, and may react to crosslink polymer chains.

In some aspects, the particulate superabsorbent polymer compositions of the present invention may be, after a heat treatment step, treated with water so that the superabsorbent polymer composition has a water content of up to about 10 wt %, or from 0.1 to about 6 wt % of the dry particulate superabsorbent polymer composition weight. This water may be added, with one or more of the surface additives from above, to the superabsorbent polymer.

The superabsorbent polymer according to the invention may be desirably prepared by two methods. The composition can be prepared continuously or discontinuously in a large-scale industrial manner, the after-crosslinking according to the invention being carried out accordingly.

According to one method, the partially neutralized monomer, such as acrylic acid, is converted into a gel by free-radical polymerization in aqueous solution in the presence of crosslinking agents and any further components, and the gel is comminuted, dried, ground, and sieved off to the desired particle size. This polymerization can be carried out continuously or discontinuously. For the present invention, the size of the high-capacity superabsorbent polymer composition particles is dependent on manufacturing processes including milling and sieving. It is well known to those skilled in the art that particle size distribution of the superabsorbent polymer particles resembles a normal distribution or a bell shaped curve. It is also known that for various reasons, the normal distribution of the particle size distribution may be skewed in either direction.

According to another method, inverse suspension and emulsion polymerization can also be used for preparation of the products according to the invention. According to these processes, an aqueous, partly neutralized solution of monomer, such as acrylic acid, is dispersed in a hydrophobic, organic solvent with the aid of protective colloids and/or emulsifiers, and the polymerization is started by free radical initiators. The internal crosslinking agents may be either dissolved in the monomer solution and are metered in together with this, or are added separately and optionally during the polymerization. The addition of a water-soluble polymer as the graft base optionally takes place via the monomer solution or by direct introduction into the oily phase. The water is then removed azeotropically from the mixture, and the polymer is filtered off and optionally dried. Internal crosslinking can be carried out by polymerizing-in a polyfunctional crosslinking agent dissolved in the monomer solution and/or by reaction of suitable crosslinking agents with functional groups of the polymer during the polymerization steps.

The result of these methods is a superabsorbent polymer or a superabsorbent polymer preproduct. A superabsorbent polymer preproduct as used herein is produced by repeating all of the steps for making the superabsorbent, up to and including drying the material, and coarse grinding in a crusher, and removing particles greater than about 850 μm and smaller than about 150 μm.

The particulate superabsorbent polymer composition of the present invention exhibits certain characteristics, or properties, as measured by Centrifuge Retention Capacity(CRC), Absorbency Under Load at about 0.9 psi (AUL(0.9 psi)), and Gel Bed Permeability(GBP).

The resultant CRC of the particulate superabsorbent polymer composition is stated as grams of liquid retained per gram weight of the sample (g/g) and may be from about 20 g/g to 40 g/g, from about 22 g/g to about 35 g/g, or from about 24 g/g to about 30 g/g or from about 25 g/g to about 30 g/g as determined by the Centrifuge Retention Capacity Test set forth herein.

The Absorbency Under Load at about 0.9 psi (AUL(0.9 psi)) of the particulate superabsorbent polymer composition may range from about 12 g/g to about 30 g/g, or from about 16 g/g to about 25 g/g as determined by the Absorbency Under Load(0.9 psi) Test set forth herein.

The Gel Bed Permeability(GBP) of the particulate superabsorbent polymer composition may be at least about 5 Darcy, or from about 5 Darcy to about 300 Darcy, or from about 20 Darcy to about 200 Darcy, or from about 20 Darcy to about 150 Darcy, or from about 50 Darcy to about 150 Darcy as determined by the Free-Swell Gel Bed Permeability Test set forth herein.

The residual glycidyl in the particulate superabsorbent polymer composition may be less than 500 ppm, or less than 100 ppm, or less than about 5 ppm or less based on the mass of the internal crosslinker composition as determined by the Glycidyl Compound in Amine-Glycidyl Compound Reaction Products Test set forth herein.

The Absorption at Pressure at 0.7 psi (AAP(0.7 psi)) may range from about 15 g/g to about 40 g/g as determined by the Absorbency At Pressure at 0.7 psi Test as set forth herein.

The permeability as measured by the Saline Flow Conductivity (SFC) test may range from about $20 \times 10^{-7}$ cm sec/g to about $200 \times 10^{-7}$ cm sec/g as determined by the Saline Flow Conductivity (SFC) Test as set forth herein.

The superabsorbent polymer compositions according to the present invention can be employed in many absorbent articles including sanitary towels, diapers, or wound coverings, and they have the property that they rapidly absorb large amounts of menstrual blood, urine, or other body fluids. Since the agents according to the invention retain the absorbed liquids even under pressure and are also capable of distributing further liquid within the construction in the swollen state, they are more desirably employed in higher concentrations, with respect to the hydrophilic fiber material, such as fluff, when compared to conventional current superabsorbent compositions. They are also suitable for use as a homogeneous superabsorber layer without fluff content within the diaper construction, as a result of which particularly thin articles are possible. The polymers are furthermore suitable for use in hygiene articles (incontinence products) for adults.

Absorbent articles, like diapers, may include (a) a liquid pervious topsheet; (b) a liquid impervious backsheet; (c) a core positioned between (a) and (b) and comprising about 10% to 100%, and preferably about 50% to about 100%, by weight of the particulate superabsorbent polymer composition, and 0% to 90% by weight of hydrophilic fiber material; (d) optionally a tissue layer positioned directly above and below said core (c); and (e) optionally an acquisition layer positioned between (a) and (c).

Test Procedures

Centrifuge Retention Capacity Test (CRC).

The CRC Test measures the ability of the superabsorbent polymer to retain liquid therein after being saturated and subjected to centrifugation under controlled conditions. The resultant retention capacity is stated as grams of liquid retained per gram weight of the sample, (g/g).

The CRC may be determined in accordance with ERT 441.2-02, which is incorporated by reference, "ERT" representing "EDANA recommended Test" and "EDANA" representing European Disposables and Nonwovens Association or as follows.

The CRC is measured by placing about 0.16 grams of the pre-screened superabsorbent polymer sample into a water-permeable bag that will contain the sample while allowing a test solution (0.9 weight percent sodium chloride in distilled water) to be freely absorbed by the sample. A heat-sealable tea bag material, such as that available from Dexter Corporation (having a place of business in Windsor Locks, Conn., U.S.A.) as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals are about 0.25 inches inside the edge of the material. After the sample is placed in the pouch, the remaining open edge of the pouch is also heat-sealed. Empty bags are also made to serve as controls. Three samples are prepared for each superabsorbent polymer composition to be tested.

The sealed bags are submerged in a pan containing the test solution at an assigned testing temperature, making sure that the bags are held down until they are completely wetted. After wetting, the samples remain in the solution for an assigned period of testing time, at which time they are removed from the solution and temporarily laid on a non-absorbent flat surface.

The wet bags are then placed into the basket wherein the wet bags are separated from each other and are placed at the outer circumferential edge of the basket, wherein the basket is of a suitable centrifuge capable of subjecting the samples to a g-force of about 350. One suitable centrifuge is a CLAY ADAMS DYNAC II, model #0103, having a water collection basket, a digital rpm gauge, and a machined drainage basket adapted to hold and drain the flat bag samples. Where multiple samples are centrifuged, the samples are placed in opposing positions within the centrifuge to balance the basket when spinning. The bags (including the wet, empty bags) are centrifuged at about 1,600 rpm (e.g., to achieve a target g-force of about 350 g force with a variance from about 240 to about 360 g force), for 3 minutes. G force is defined as an unit of inertial force on a body that is subjected to rapid acceleration or gravity, equal to 32 ft/sec$^2$ at sea level. The bags are removed and weighed, with the empty bags (controls) being weighed first, followed by the bags containing the superabsorbent polymer composition samples. The amount of solution retained by the superabsorbent polymer sample, taking into account the solution retained by the bag itself, is the centrifuge retention capacity (CRC) of the superabsorbent polymer, expressed as grams of fluid per gram of superabsorbent polymer. More particularly, the retention capacity is determined by the following equation:

$$CRC = [sample\ bag\ after\ centrifuge - empty\ bag\ after\ centrifuge - dry\ sample\ weight] / dry\ sample\ weight$$

The three samples are tested, and the results are averaged to determine the CRC of the superabsorbent polymer composition.

Glycidyl Compound in Amine-Glycidyl Compound Reaction Products Test

This method is applied to amine-glycidyl compound reaction products for the analysis of free allyl glycidyl compound above 20 ppm. An example of a glycidyl compound is allylglycidyl ether (AGE), which will be used herein. Gas chromatographic separation (GLC) was used. The AGE content is determined by GLC using a flame ionization detector (FID). The AGE is quantified against ethylhexyl glycidyl ether (EHGE) as an internal standard.

40 mg of EHGE is dissolved 100 ml of methylene chloride to form a EHGE solution. 100 mg of AGE was measured into an autosampler vial. 1 ml of EHGE solution was added to the sample. 1 µl of the sample was injected into the GLC.

Calibration—25 mg of AGE is dissolved in 20 ml of methylene chloride. 10, 50, and 100 µl of the AGE stock was transferred into the sampler vial. 1 ml of the internal standard solution to each sample. Inject 1 µl of the sample into the GLC.

GLC analysis is carried out with a GLC equipped with a split/splitless injector, capillary column and a flame ionization. Conditions include Injector—290° C. split 30 ml
Injection volume 1 µl
Column—50 m 0.32 mm HP5 dF 1.0 µm
Carrier gas—helium, constant flow 2 ml/min
Temperature program—80° C.-200° C. with 8° C./min; then 200° C.-300° C. with 30° C./min(conditioning)
Detector—FID at 310° C.
Hydrogen 40 ml/min
Air 400 ml/min
Make up gas—12 ml/min.

The retention lines of AGE and EHGE is verified by analysis of the pure AGE and EHGE. From the peak areas, an internal standard calibration function of the amount of AGE vs. the amount of EHGE is established with $$\{A_{AGE(C)}/A_{EHGE(C)}\} = \alpha_1 * \{C_{AGE(C)}/A_{EHGE(C)}\} + 0$$

wherein
$A_{AGE(C)}$ is the area in the calibration sample;
$A_{EHGE(C)}$ is the area in the calibration sample;
$C_{AGE}(C)$ is the concentration of AGE in the calibration sample in µg.;
$C_{EHGE(C)}$ is the concentration of EHGE in the calibration sample in µg; and
$\alpha_1$ is the slope of the function.

Using this calculation function, the content of ACE in the samples is calculated as mg/kg samples (ppm).

Free-Swell Gel Bed Permeability Test (FSGBP)

Figure 2:
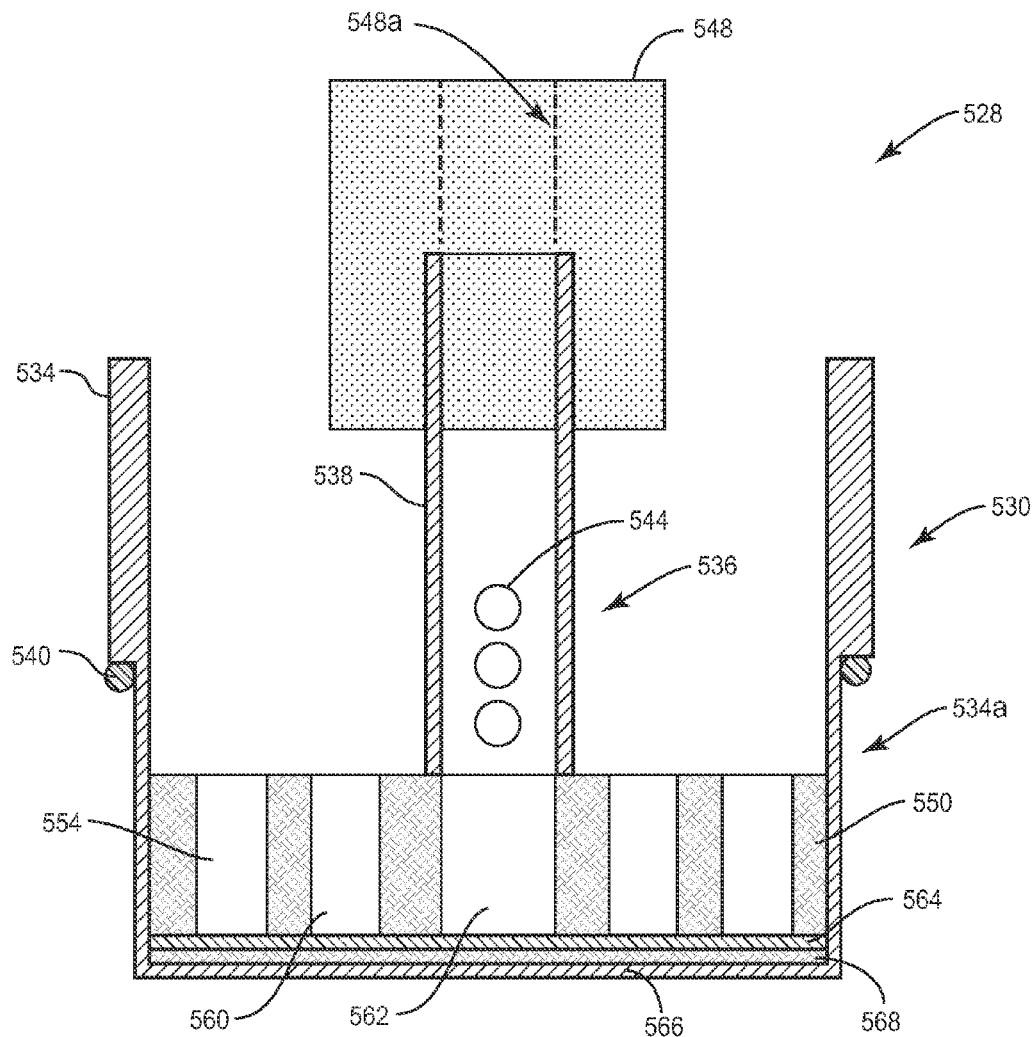
FIG. 2 is a cross-sectional side view of a cylinder/cup assembly employed in the Free Swell Gel Bed Permeability Test apparatus shown in FIG. 1.
Figure 3:
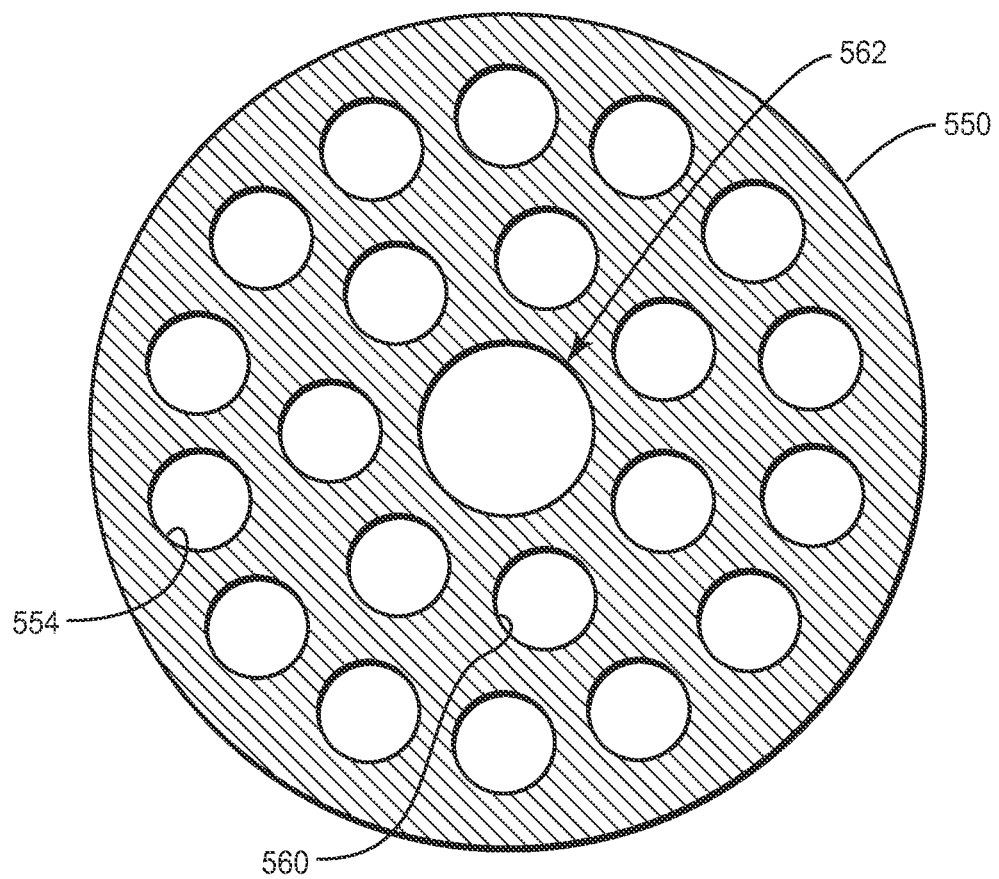
FIG. 3 is a top view of a plunger employed in the Free Swell Gel Bed Permeability Test apparatus shown in FIG. 1.

As used herein, the Free-Swell Gel Bed Permeability Test, also referred to as the Gel Bed Permeability (GBP) Under 0 psi Swell Pressure Test, determines the permeability of a swollen bed of gel particles (e.g., such as the surface treated absorbent material or the superabsorbent material prior to being surface treated), under what is commonly referred to as "free swell" conditions. The term "free swell" means that the gel particles are allowed to swell without a restraining load upon absorbing test solution as will be described. A suitable apparatus for conducting the Gel Bed Permeability Test is shown in FIGS. 1, 2, and 3 and indicated generally as 500. The test apparatus assembly 528 comprises a sample container, generally indicated at 530, and a plunger, generally indicated at 536. The plunger comprises a shaft 538 having a cylinder hole bored down the longitudinal axis and a head 550 positioned at the bottom of the shaft. The shaft hole 562 has a diameter of about 16 mm. The plunger head is attached to the shaft, such as by adhesion. Twelve holes 544 are bored into the radial axis of the shaft, three positioned at every 90 degrees having diameters of about 6.4 mm. The shaft 538 is machined from a LEXAN rod or equivalent material and has an outer diameter of about 2.2 cm and an inner diameter of about 16 mm.

The plunger head 550 has a concentric inner ring of seven holes 560 and an outer ring of 14 holes 554, all holes having a diameter of about 8.8 millimeters as well as a hole of about 16 mm aligned with the shaft. The plunger head 550 is machined from a LEXAN rod or equivalent material and has a height of approximately 16 mm and a diameter sized such that it fits within the cylinder 534 with minimum wall clearance but still slides freely. The total length of the plunger head 550 and shaft 538 is about 8.25 cm, but can be machined at the top of the shaft to obtain the desired mass of the plunger 536. The plunger 536 comprises a 100 mesh stainless steel cloth screen 564 that is biaxially stretched to tautness and attached to the lower end of the plunger 536. The screen is attached to the plunger head 550 using an appropriate solvent that causes the screen to be securely adhered to the plunger head 550. Care must be taken to avoid excess solvent migrating into the open portions of the screen and reducing the open area for liquid flow. Acrylic solvent Weld-on 4 from IPS Corporation (having a place of business in Gardena, Calif., USA) is a suitable solvent.

The sample container 530 comprises a cylinder 534 and a 400 mesh stainless steel cloth screen 566 that is biaxially stretched to tautness and attached to the lower end of the cylinder 534. The screen is attached to the cylinder using an appropriate solvent that causes the screen to be securely adhered to the cylinder. Care must be taken to avoid excess solvent migrating into the open portions of the screen and reducing the open area for liquid flow. Acrylic solvent Weld-on 4 from IPS Corporation (having a place of business in Gardena, Calif., USA) is a suitable solvent. A gel particle sample, indicated as 568 in FIG. 2, is supported on the screen 566 within the cylinder 534 during testing.

The cylinder 534 may be bored from a transparent LEXAN rod or equivalent material, or it may be cut from a LEXAN tubing or equivalent material, and has an inner diameter of about 6 cm (e.g., a cross-sectional area of about 28.27 cm$^2$), a wall thickness of about 0.5 cm and a height of approximately 7.95 cm. A step is machined into the outer diameter of the cylinder 534 such that a region 534a with an outer diameter of 66 mm exists for the bottom 31 mm of the cylinder 534. An o-ring 540 which fits the diameter of region 534a may be placed at the top of the step.

The annular weight 548 has a counter-bored hole about 2.2 cm in diameter and 1.3 cm deep so that it slips freely onto the shaft 538. The annular weight also has a thru-bore 548a of about 16 mm. The annular weight 548 can be made from stainless steel or from other suitable materials resistant to corrosion in the presence of the test solution, which is 0.9 weight percent sodium chloride solution in distilled water. The combined weight of the plunger 536 and annular weight 548 equals approximately 596 grams (g), which corresponds to a pressure applied to the sample 568 of about 0.3 pounds per square inch (psi), or about 20.7 dynes/cm$^2$ (2.07 kPa), over a sample area of about 28.27 cm$^2$.

When the test solution flows through the test apparatus during testing as described below, the sample container 530 generally rests on a weir 600. The purpose of the weir is to divert liquid that overflows the top of the sample container 530 and diverts the overflow liquid to a separate collection device 601. The weir can be positioned above a scale 602 with a beaker 603 resting on it to collect saline solution passing through the swollen sample 568.

To conduct the Gel Bed Permeability Test under "free swell" conditions, the plunger 536, with the weight 548 seated thereon, is placed in an empty sample container 530 and the height from the top of the weight 548 to the bottom of the sample container 530 is measured using a suitable gauge accurate to 0.01 mm. The force the thickness gauge applies during measurement should be as low as possible, preferably less than about 0.74 Newtons. It is important to measure the height of each empty sample container 530, plunger 536, and weight 548 combination and to keep track of which plunger 536 and weight 548 is used when using multiple test apparatus. The same plunger 536 and weight 548 should be used for measurement when the sample 568 is later swollen following saturation. It is also desirable that the base that the sample cup 530 is resting on is level, and the top surface of the weight 548 is parallel to the bottom surface of the sample cup 530.

The sample to be tested is prepared from superabsorbent polymer composition particles which are prescreened through a U.S. standard 30 mesh screen and retained on a U.S. standard 50 mesh screen. As a result, the test sample comprises particles sized in the range of about 300 to about 600 microns. The superabsorbent polymer particles can be pre-screened with, for example, a RO-TAP Mechanical Sieve Shaker Model B available from W. S. Tyler, Inc., Mentor Ohio. Sieving is conducted for 10 minutes. Approximately 2.0 grams of the sample is placed in the sample container 530 and spread out evenly on the bottom of the sample container. The container, with 2.0 grams of sample in it, without the plunger 536 and weight 548 therein, is then submerged in the 0.9% saline solution for a time period of about 60 minutes to saturate the sample and allow the sample to swell free of any restraining load. During saturation, the sample cup 530 is set on a mesh located in the liquid reservoir so that the sample cup 530 is raised slightly above the bottom of the liquid reservoir. The mesh does not inhibit the flow of saline solution into the sample cup 530. A suitable mesh can be obtained as part number 7308 from Eagle Supply and Plastic, having a place of business in Appleton, Wis., U.S.A. Saline does not fully cover the superabsorbent polymer composition particles, as would be evidenced by a perfectly flat saline surface in the test cell. Also, saline depth is not allowed to fall so low that the surface within the cell is defined solely by swollen superabsorbent, rather than saline.

At the end of this period, the plunger 536 and weight 548 assembly is placed on the saturated sample 568 in the sample container 530 and then the sample container 530, plunger 536, weight 548, and sample 568 are removed from the solution. After removal and before being measured, the sample container 530, plunger 536, weight 548, and sample 568 are to remain at rest for about 30 seconds on a suitable flat, large grid non-deformable plate of uniform thickness. The thickness of the saturated sample 568 is determined by again measuring the height from the top of the weight 548 to the bottom of the sample container 530, using the same thickness gauge used previously provided that the zero point is unchanged from the initial height measurement. The sample container 530, plunger 536, weight 548, and sample 568 may be placed on a flat, large grid non-deformable plate of uniform thickness that will provide for drainage. The plate has an overall dimension of 7.6 cm by 7.6 cm, and each grid has a cell size dimension of 1.59 cm long by 1.59 cm wide by 1.12 cm deep. A suitable flat, large grid non-deformable plate material is a parabolic diffuser panel, catalogue number 1624K27, available from McMaster Carr Supply Company, having a place of business in Chicago, Ill., U.S.A., which can then be cut to the proper dimensions. This flat, large mesh non-deformable plate must also be present when measuring the height of the initial empty assembly. The height measurement should be made as soon as practicable after the thickness gauge is engaged. The height measurement obtained from measuring the empty sample container 530, plunger 536, and weight 548 is subtracted from the height measurement obtained after saturating the sample 568. The resulting value is the thickness, or height "H" of the swollen sample.

The permeability measurement is initiated by delivering a flow of the 0.9% saline solution into the sample container 530 with the saturated sample 568, plunger 536, and weight 548 inside. The flow rate of test solution into the container is adjusted to cause saline solution to overflow the top of the cylinder 534 thereby resulting in a consistent head pressure equal to the height of the sample container 530. The test solution may be added by any suitable means that is sufficient to ensure a small, but consistent amount of overflow from the top of the cylinder, such as with a metering pump 604. The overflow liquid is diverted into a separate collection device 601. The quantity of solution passing through the sample 568 versus time is measured gravimetrically using the scale 602 and beaker 603. Data points from the scale 602 are collected every second for at least sixty seconds once the overflow has begun. Data collection may be taken manually or with data collection software. The flow rate, Q, through the swollen sample 568 is determined in units of grams/second (g/s) by a linear least-square fit of fluid passing through the sample 568 (in grams) versus time (in seconds).

Permeability in $cm^2$ is obtained by the following equation:

$$K=[Q*H*\mu]/[A*\rho*P]$$

where K=Permeability ($cm^2$), Q=flow rate (g/sec), H=height of swollen sample (cm), $\mu$=liquid viscosity (poise) (approximately one centipoise for the test solution used with this Test), A=cross-sectional area for liquid flow (28.27 $cm^2$ for the sample container used with this Test), $\rho$=liquid density ($g/cm^3$) (approximately one $g/cm^3$, for the test solution used with this Test) and P=hydrostatic pressure ($dynes/cm^2$) (normally approximately 7,797 $dynes/cm^2$). The hydrostatic pressure is calculated from $P=\rho*g*h$, where $\rho$=liquid density ($g/cm^3$), g=gravitational acceleration, nominally 981 $cm/sec^2$, and h=fluid height, e.g., 7.95 cm for the Gel Bed Permeability Test described herein.

A minimum of two samples is tested and the results are averaged to determine the gel bed permeability of the sample.

Absorbency Under Load Test (AUL(0.9 psi))

The Absorbency Under Load (AUL) Test measures the ability of the superabsorbent polymer composition particles to absorb a 0.9 weight percent solution of sodium chloride in distilled water at room temperature (test solution) while the material is under a 0.9 psi load. The apparatus for testing AUL consists of:

An AUL assembly including a cylinder, a 4.4 g piston, and a standard 317 gm weight. The components of this assembly are described in additional detail below.

A flat-bottomed square plastic tray that is sufficiently broad to allow the glass frits to lay on the bottom without contact with the tray walls. A plastic tray that is 9" by 9"(22.9 cm×22.9 cm), with a depth of 0.5 to 1"(1.3 cm to 2.5 cm) is commonly used for this test method.

A 9 cm diameter sintered glass frit with a 'C' porosity (25-50 microns). This frit is prepared in advance through equilibration in saline (0.9% sodium chloride in distilled water, by weight). In addition to being washed with at least two portions of fresh saline, the frit must be immersed in saline for at least 12 hours prior to AUL measurements.

Whatman Grade 1, 9 cm diameter filter paper circles.

A supply of saline (0.9% sodium chloride in distilled water, by weight).

Figure 4:
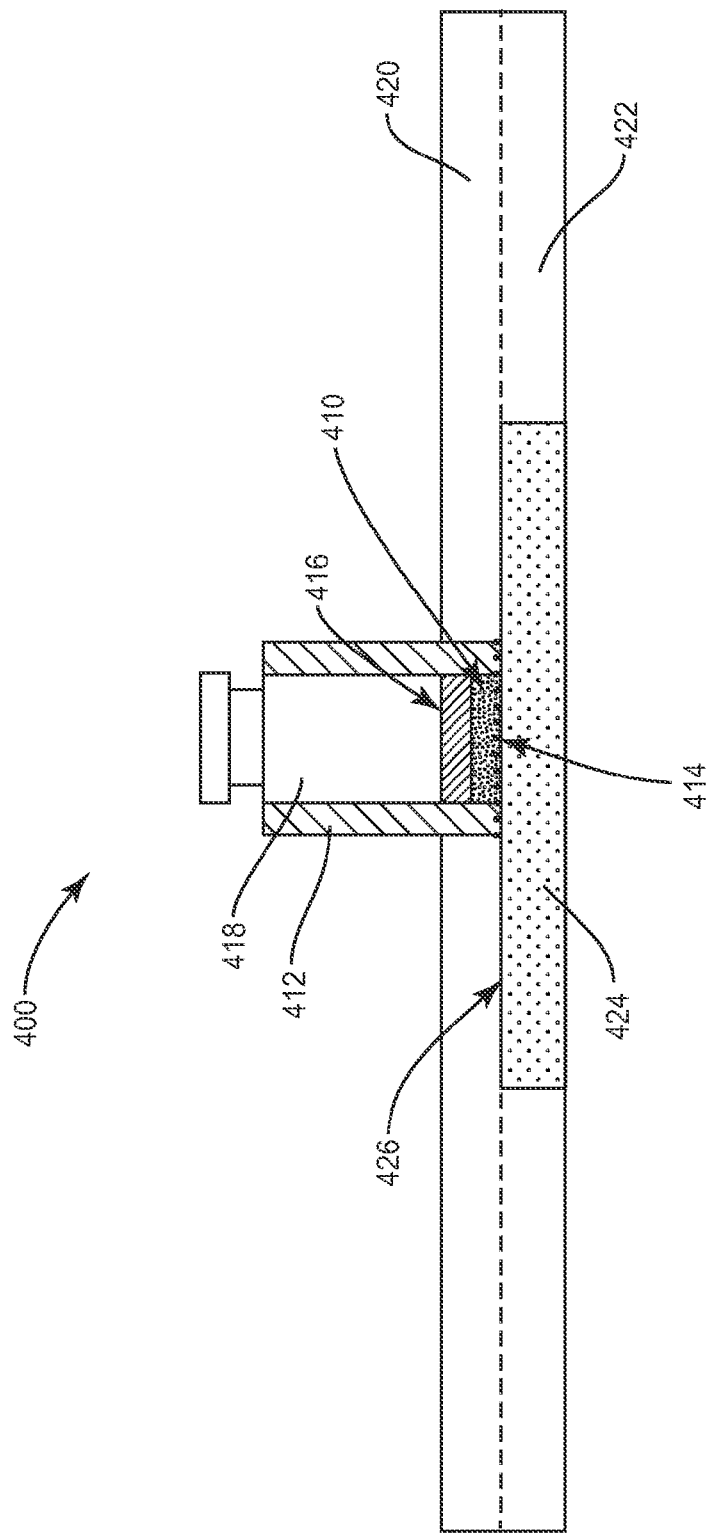
FIG. 4 is a side view of the test apparatus employed for the Absorbency Under Load Test.

Referring to FIG. 4, the cylinder 412 of the AUL assembly 400 used to contain the superabsorbent polymer composition particles 410 is made from one-inch (2.54 cm) inside diameter thermoplastic tubing machined-out slightly to be sure of concentricity. After machining, a 400 mesh stainless steel wire cloth 414 is attached to the bottom of the cylinder 412 by heating the steel wire cloth 414 in a flame until red hot, after which the cylinder 412 is held onto the steel wire cloth until cooled. A soldering iron can be utilized to touch up the seal if unsuccessful or if it breaks. Care must be taken to maintain a flat smooth bottom and not distort the inside of the cylinder 412.

The 4.4 g piston (416) is made from one-inch diameter solid material (e.g., PLEXIGLAS®) and is machined to closely fit without binding in the cylinder 412.

A standard 317 gm weight 418 is used to provide a 62,053 dyne/cm$^2$ (about 0.9 psi) restraining load. The weight is a cylindrical, 1 inch(2.5 cm) diameter, stainless steel weight that is machined to closely fit without binding in the cylinder.

Unless specified otherwise, a sample 410 corresponding to a layer of at least about 300 gsm. (0.16 g) of superabsorbent polymer composition particles is utilized for testing the AUL. The sample 410 is taken from superabsorbent polymer composition particles that are pre-screened through U.S. standard #30 mesh and retained on U.S. std. #50 mesh. The superabsorbent polymer composition particles can be pre-screened with, for example, a RO-TAP® Mechanical Sieve Shaker Model B available from W. S. Tyler, Inc., Mentor Ohio. Sieving is conducted for about 10 minutes.

The inside of the cylinder 412 is wiped with an antistatic cloth prior to placing the superabsorbent polymer composition particles 410 into the cylinder 412.

The desired amount of the sample of sieved superabsorbent polymer composition particles 410 (about 0.16 g) is weighed out on a weigh paper and evenly distributed on the wire cloth 414 at the bottom of the cylinder 412. The weight of the superabsorbent polymer composition particles in the bottom of the cylinder is recorded as 'SA,' for use in the AUL calculation described below. Care is taken to be sure no superabsorbent polymer particles cling to the wall of the cylinder. After carefully placing the 4.4 g piston 412 and 317g weight 418 on the superabsorbent polymer composition particles 410 in the cylinder 412, the AUL assembly 400 including the cylinder, piston, weight, and superabsorbent polymer composition particles is weighed, and the weight is recorded as weight 'A'.

A sintered glass frit 424 (described above) is placed in the plastic tray 420, with saline 422 added to a level equal to that of the upper surface of the glass frit 424. A single circle of filter paper 426 is placed gently on the glass frit 424, and the AUL assembly 400 with the superabsorbent polymer composition particles 410 is then placed on top of the filter paper 426. The AUL assembly 400 is then allowed to remain on top of the filter paper 426 for a test period of one hour, with attention paid to keeping the saline level in the tray constant. At the end of the one hour test period, the AUL apparatus is then weighed, with this value recorded as weight 'B.'

The AUL(0.9 psi) is calculated as follows:

$AUL(0.9psi)=(B-A)/SA$ wherein
A=Weight of AUL Unit with dry SAP
B=Weight of AUL Unit with SAP after 60 minutes absorption
SA=Actual SAP weight A minimum of two tests is performed and the results are averaged to determine the AUL value under 0.9 psi load. The samples are tested at about 23° C. and about 50% relative humidity.

Absorption at Pressure at 0.7 psi (AAP(0.7 psi)

The absorption at pressure (pressure load 50 g/cm.sup.2) is determined by a method described in EP 0 339 461, p. 7 wherein the absorption at pressure as set forth in EP 0 339 461 on page 7 is incorporated by reference into the present application. Approximately 0.9 g superabsorber is weighed into a cylinder with a sieve plate. The uniformly scattered superabsorber layer is placed under load in the form of a plunger exerting a pressure of 0.7 psi or 50 g/cm$^2$. The pre-weighed cylinder is then placed on a glass filter disk standing in a bowl containing 0.9% NaCl solution, the liquid level of which corresponds precisely to the height of the filter disk. After the cylinder unit has been left to soak up 0.9% NaCl solution for 1 hour, this is re-weighed, and the AAP is calculated as follows: AAP=amount weighed out (cylinder unit+superabsorber)-amount weighed in (cylinder unit+superabsorber soaked to capacity)/amount of superabsorber weighed in.

Saline Flow Conductivity (SFC) Test

Permeability to a 0.9% Common Salt Solution in the Swollen State (SFC)

Permeability in the swollen state (SFC test, according to WO 95/22356 wherein the SFC test as set forth in WO 95/22356 is incorporated by reference into the present application). Approximately 0.9 g superabsorber material is weighed into a cylinder having a sieve plate and is distributed carefully on the surface of the sieve. The superabsorber material is allowed to swell for 1 hour against an opposing pressure of 20 g/cm$^2$ in JAYCO synthetic urine [composition: 2.0 g potassium chloride; 2.0 g sodium sulfate; 0.85 g ammonium dihydrogen phosphate; 0.15 g ammonium hydrogen phosphate; 0.19 g calcium chloride; 0.23 g magnesium chloride as anhydrous salts dissolved in 1 liter distilled water]. After determining the swollen height of the superabsorber, 0.118 M NaCl solution are run through the swollen gel layer from a leveled supply vessel at constant hydrostatic pressure. The swollen gel layer is covered during measurement with a special sieve cylinder which guarantees a uniform distribution of the 0.118 M NaCl solution above the gel and constant conditions (measuring temperature 20-25° C.) during measurement in relation to the gel bed state. The pressure acting on the swollen superabsorber continues at 20 g/cm$^2$. With the aid of a computer and scales the quantity of liquid which passes through the gel layer as a function of time is determined at 20-second intervals within a period of 10 minutes. Using regression analysis, the flow rate, g/s, through the swollen gel layer at t=0 is determined at the mid-point of the flow quantity between minutes 2 and 10 by extrapolation of the gradient.

The SFC value (K) is calculated as follows:

$$K=F_s(t=0)\cdot L_o/(r\cdot A\cdot \Delta P)=F_s(t=0)\cdot L_o/(139506)$$

wherein: $F_s(t=0)$ flow rate in g/s
$L_0$ is the thickness of the gel layer, in cm
r is the density of the NaCl solution (1.003 g/cm$^3$)
A is the area of the upper surface of the gel layer in the measuring cylinder (28.27 cm$^2$)
$\Delta P$ is the hydrostatic pressure bearing on the gel layer (4920 dyne/cm$^2$) and
K is the SFC value [$10^{-7}*cm^3*s*g^{-1}$].

EXAMPLES

The following Internal Crosslinkers 1-3, Comparative Internal Crosslinkers C1-C4, Particulate Superabsorbent Polymer Composition, and Examples 1-60 are provided to illustrate the inventions of products including crosslinker compositions, superabsorbent polymer, particulate superabsorbent polymer, and particulate superabsorbent polymer compositions, and processes to make these products as set forth in the claims, and do not limit the scope of the claims. Unless otherwise stated all parts, and percentages are based on the dry particulate superabsorbent polymer composition. The term Comparative Internal Crosslinker is meant to depict crosslinkers that are not part of the present invention.

The term Internal Crosslinker as used in the examples will refer to one of the following which are crosslinker compositions of the present invention:

Internal Crosslinker 1: Ethylenediamine-AGE Adduct

A 1 L reaction vessel equipped with an agitator, heating and cooling facilities and a vacuum system is purged with nitrogen. Ethylenediamine (60.1 g) and water (10.0 g) are charged into the reactor and heated to 80° C. Allylglycidyl ether (423.0 g) is added within 75 min at 80° C. under agitation and cooling. After 4 hours of post reaction the mixture is heated to 110° C. Water is distilled off under vacuum (20 mbar), and the final product is cooled to room temperature. The clear and slightly yellow product is an adduct of ethylenediamine with 3.7 mol allylglycidyl ether is a crosslinker composition of the present invention. The product contains 5.74 weight-% of nitrogen and less than 30 ppm of allylglycidyl ether.

Internal Crosslinker 2: Ethylenediamine-AGE-PO Adduct

A 1 L reaction autoclave equipped with an agitator, heating and cooling facilities and a vacuum system is purged with nitrogen. Ethylenediamine (60.1 g) and water (10.0 g) are charged into the reactor and heated to 80° C. Allylglycidyl ether (423.0 g) is added within 75 min at 80° C. under agitation and cooling. After 4 hours of post reaction propylene oxide (27.4 g) is charged into the vessel within 2 min. The mixture is agitated at 80° C. for 75 min, then heated to 110° C. Water and unreacted propylene oxide are distilled off under vacuum (20 mbar), and the final product is cooled to room temperature. The clear and slightly yellow product is an adduct of ethylenediamine with 3.7 mol allylglycidyl ether and 0.3 mol propylene oxide is a crosslinker composition of the present invention. The product contains 5.60 weight-% of nitrogen and less than 30 ppm of allylglycidyl ether.

Comparative Internal Crosslinker 1: Ethylenediamine-AGE Adduct

The procedure described in example 1 is repeated. Ethylenediamine (60.1 g) and water (10.0 g) are reacted with allylglycidyl ether (456.2 g) at 80° C. The clear and slightly yellow product is an adduct of ethylenediamine with 4.0 mol allylglycidyl ether. The product contains 2400 ppm allylglycidyl ether.

Internal Crosslinker 3 (Ethylenediamine-AGE-PO Adduct

A 1 L reaction autoclave equipped with an agitator, heating and cooling facilities and a vacuum system is purged with nitrogen. Allylglycidylether (243 g) and water (5.7 g) are charged into a 1 L autoclave. The mixture is heated to 80° C. under inert conditions. Ethylenediamine (34.5 g) are added at 80° C. and at standard pressure within 30 min using a dropping funnel. Cooling is applied to keep the reaction temperature at 80° C. After 4 hours of post reaction and agitation the reaction mixture is cooled to less than 50° C. and removed from the reactor.

The reactor is cleaned by purging and boiling with acetone. Finally residual acetone is removed by heating under vacuum. The reaction mixture is transferred back into the reactor from which all remaining AGE had been removed. The autoclave is again purged with nitrogen and the reaction mixture heated to 80° C. PO (17 g) is quickly charged at 80° C. within 1 min. After a post reaction of 75 min at 80° C. unreacted PO and water are distilled off at 115° C. under vacuum. Finally the product is cooled to 50° C. and removed from the vessel. The clear and slightly yellow product is an adduct of ethylenediamine with 3.7 mol allylglycidyl ether and 0.3 mol propylene oxide. The product contains 73 ppm allylglycidyl ether.

Particulate Superabsorbent Polymer Composition

A superabsorbent polymer according to the present invention is made in the following way. A monomer solution consisting of 640 g of acrylic acid, of which 75 mol % have been neutralized with sodium hydroxide solution (532.82 g of 50% NaOH), 801.32 g of water, 1.92 g of an Internal Crosslinker as set forth in Tables 2-6 for Examples 1-100, is freed of dissolved oxygen by flushing with nitrogen and cooled to the starting temperature of 4° C. After the starting temperature has been reached, the initiator solution (0.6 g of sodium peroxydisulfate in 10 g of $H_2O$, 0.014 g of 35% hydrogen peroxide solution in 10 g of $H_2O$ and 0.03 g of ascorbic acid in 2 g of $H_2O$) was added. Once the final temperature of about 100° C. had been reached, the resulting gel was comminuted using a mincer and dried at 150° C. for 2 hours in a drying cabinet.

A particulate superabsorbent polymer composition of the present invention is prepared when the dried polymerizate was coarsely pounded, ground using a cutting mill SM 100 having 2 mm Conidur holes and screened to a powder having a particle size of from 150 to 850 µm, thus yielding powder A (particle sizes: on 150 µm mesh size 13%, on 300 µm mesh size 15%, on 400 µm mesh size 13%, on 500 µm mesh size 15%, on 600 µm mesh size 20%, on 710 to 850 µm mesh size 24%). The particulate superabsorbent polymer composition has CRC of about 33 g/g. The particulate superabsorbent polymer composition was surface treated as set forth in Examples 1-80 resulting in the particulate superabsorbent polymer composition of the present invention.

Examples 1-80

The following examples shown in Tables 2-5 represent embodiments of the particulate superabsorbent polymer composition of the present invention wherein the Internal Crosslinkers set forth above are used in the Particulate Superabsorbent Polymer Composition wherein the particulate superabsorbent polymer has been further treated with surface crosslinking and optionally surface treatment as shown in the tables below and described herein to make the particulate superabsorbent polymer composition. All of the examples are surface crosslinked with a solution comprising 1 wt % ethylene carbonate and 3 wt % water along with other ingredients as shown in the tables and heat treated as depicted in the summary before each table.

The following nomenclature is used in the following tables: SX means surface crosslink; Pre-treatment before SX means application of elements onto the particle surface; Post-treatment after SX means surface treatment of the surface crosslinked superabsorbent polymer particles; and EC means ethylene carbonate. The units of the Properties are CRC (g/g); AUL(0.9 psi) (g/g); GBP (Darcy); AAP(0.7 psi) (g/g) and SFC ($10^{-7}*cm^3*s*g^{-1}$). All % in the table means wt % as defined herein. The silica used in the examples is SIPERNAT® 22S; the aluminum sulfate is $Al_2(SO_4)_3 \times 14\ H_2O$.

TABLE 2

(1 molEDA + 3.7 molAGE) Examples 1-20 of Particulate Superabsorbent Polymer Composition including Internal Crosslinker 1.

1.92 g of Internal Crosslinker 1 was added to the solution as set forth in making the Particulate Superabsorbent Polymer Composition and the resulting particulate superabsorbent polymer was surface crosslinked and surface treated as set forth in Table 2 to form Examples 1-20 of the particulate superabsorbent polymer composition.

| | | Pre-Treatment before SX | | | | SX step | | Post-treatment after SX | | | | Properties | | | | |
|---|---|---|---|---|---|---|---|---|---|---|---|---|---|---|---|---|
| No. | EC | Water | Silica | Al-lactate | Al-Sulfate | Temperature | Time min | Water | Silica | Al-lactate | Al-Sulfate | CRC | AUL (0.9 psi) | GBP | AAP (0.7 psi) | SFC |
| 1 | 1% | 3% | — | 0.3% | — | 180° C. | 30 | — | — | — | — | 26.6 | 22.9 | 14 | 23.3 | 70 |
| 2 | 1% | 3% | — | 0.3% | — | 170° C. | 90 | — | — | — | — | 27.9 | 23.1 | 13 | 24.0 | 45 |
| 3 | 1% | 3% | — | — | 0.3% | 180° C. | 30 | — | — | — | — | 26.5 | 22.7 | 25 | 22.5 | 69 |
| 4 | 1% | 3% | — | — | 0.3% | 170° C. | 90 | — | — | — | — | 25.8 | 22.7 | 33 | 23.3 | 138 |
| 5 | 1% | 3% | 0.5% | — | — | 180° C. | 30 | — | — | — | — | 26.2 | 20.9 | 90 | 21.1 | 140 |
| 6 | 1% | 3% | 0.5% | — | — | 170° C. | 90 | — | — | — | — | 26.9 | 20.5 | 94 | 21.3 | 151 |
| 7 | 1% | 3% | 0.5% | 0.3% | — | 180° C. | 30 | — | — | — | — | 26.4 | 19.4 | 87 | 20.5 | |
| 8 | 1% | 3% | 0.5% | 0.3% | — | 170° C. | 90 | — | — | — | — | 27.3 | 19.8 | 72 | 20.9 | |
| 9 | 1% | 3% | 0.5% | — | 0.3% | 180° C. | 30 | — | — | — | — | 26.8 | 19.9 | 81 | 21.0 | |
| 10 | 1% | 3% | 0.5% | — | 0.3% | 170° C. | 90 | — | — | — | — | 26.4 | 19.7 | 120 | 21.1 | |
| 11 | 1% | 3% | 0.5% | 0.15% | 0.15% | 180° C. | 30 | — | — | — | — | 27.4 | 19.9 | 91 | 20.9 | |
| 12 | 1% | 3% | 0.5% | 0.15% | 0.15% | 170° C. | 90 | — | — | — | — | 27.2 | 20.5 | 74 | 21.7 | |
| 13 | 1% | 3% | — | — | — | 180° C. | 30 | — | 0.5% | — | — | 26.9 | 23.0 | 24 | 24.1 | 46 |
| 14 | 1% | 3% | — | — | — | 170° C. | 90 | — | 0.5% | — | — | 27.3 | 23.3 | 32 | 23.4 | 68 |
| 15 | 1% | 3% | — | — | — | 180° C. | 30 | 4% | 0.5% | 0.3% | — | 26.8 | 19.4 | 72 | 20.6 | |
| 16 | 1% | 3% | — | — | — | 170° C. | 90 | 4% | 0.5% | 0.3% | — | 26.5 | 19.4 | 61 | 21.4 | |
| 17 | 1% | 3% | — | — | — | 180° C. | 30 | 4% | 0.5% | — | 0.3% | 27.1 | 19.6 | 75 | 21.2 | |
| 18 | 1% | 3% | — | — | — | 170° C. | 90 | 4% | 0.5% | — | 0.3% | 26.3 | 19.6 | 66 | 20.9 | |
| 19 | 1% | 3% | — | — | — | 180° C. | 30 | 4% | 0.5% | 0.15% | 0.15% | 26.4 | 19.9 | 50 | 21.2 | |
| 20 | 1% | 3% | — | — | — | 170° C. | 90 | 4% | 0.5% | 0.15% | 0.15% | 26.4 | 20.0 | 49 | 21.6 | |

TABLE 3

(1 molEDA + 3.7 molAGE + 0.3 mol PO) Examples 21-40 of Particulate Superabsorbent Polymer Composition including Internal Crosslinker 2.

1.92 g of Internal Crosslinker 2 was added to the solution as set forth in making the Particulate Superabsorbent Polymer Composition and the resulting particulate superabsorbent polymer was surface crosslinked and surface treated as set forth in Table 3 to form Examples 21-40 of the particulate superabsorbent polymer composition.

| | | Pre-Treatment before SX | | | | SX step | | Post-treatment after SX | | | | Properties | | | | |
|---|---|---|---|---|---|---|---|---|---|---|---|---|---|---|---|---|
| No. | EC | Water | Silica | Al-lactate | Al-Sulfate | Temperature | Time min | Water | Silica | Al-lactate | Al-Sulfate | CRC | AUL (0.9 psi) | GBP | AAP (0.7 psi) | SFC |
| 21 | 1% | 3% | — | 0.3% | — | 180° C. | 30 | — | — | — | — | 27.6 | 22.8 | 5 | 24.4 | 28 |
| 22 | 1% | 3% | — | 0.3% | — | 170° C. | 90 | — | — | — | — | 28.5 | 23.6 | 6 | 24.7 | 34 |
| 23 | 1% | 3% | — | — | 0.3% | 180° C. | 30 | — | — | — | — | 26.4 | 22.2 | 24 | 23.6 | 64 |
| 24 | 1% | 3% | — | — | 0.3% | 170° C. | 90 | — | — | — | — | 26.9 | 22.8 | 25 | 24.0 | 59 |
| 25 | 1% | 3% | 0.5% | — | — | 180° C. | 30 | — | — | — | — | 26.8 | 20.0 | 90 | 21.6 | 100 |
| 26 | 1% | 3% | 0.5% | — | — | 170° C. | 90 | — | — | — | — | 27.3 | 20.5 | 91 | 21.7 | 104 |
| 27 | 1% | 3% | 0.5% | 0.3% | — | 180° C. | 30 | — | — | — | — | 26.3 | 20.2 | 12 | 21.4 | 110 |
| 28 | 1% | 3% | 0.5% | 0.3% | — | 170° C. | 90 | — | — | — | — | 27.1 | 20.6 | 110 | 21.1 | 123 |
| 29 | 1% | 3% | 0.5% | —% | 0.3% | 180° C. | 30 | — | — | — | — | 25.9 | 20.0 | 146 | 21.3 | 246 |
| 30 | 1% | 3% | 0.5% | —% | 0.3% | 170° C. | 90 | — | — | — | — | 26.5 | 20.1 | 140 | 21.7 | 153 |
| 31 | 1% | 3% | 0.5% | 0.15% | 0.15% | 180° C. | 30 | — | — | — | — | 26.6 | 19.6 | 95 | 20.9 | 121 |
| 32 | 1% | 3% | 0.5% | 0.15% | 0.15% | 170° C. | 90 | — | — | — | — | 26.6 | 20.3 | 96 | 21.4 | 207 |
| 33 | 1% | 3% | — | — | — | 180° C. | 30 | — | 0.5% | — | — | 26.5 | 23.3 | 15 | 24.5 | 54 |
| 34 | 1% | 3% | — | — | — | 170° C. | 90 | — | 0.5% | — | — | 28.0 | 23.0 | 10 | 24.8 | 44 |
| 35 | 1% | 3% | — | — | — | 180° C. | 30 | 4% | 0.5% | 0.3% | — | 26.0 | 20.0 | 58 | 20.5 | 89 |
| 36 | 1% | 3% | — | — | — | 170° C. | 90 | 4% | 0.5% | 0.3% | — | 26.7 | 19.4 | 79 | 20.9 | 108 |
| 37 | 1% | 3% | — | — | — | 180° C. | 30 | 4% | 0.5% | — | 0.3% | 25.9 | 19.0 | 87 | 21.2 | 86 |
| 38 | 1% | 3% | — | — | — | 170° C. | 90 | 4% | 0.5% | — | 0.3% | 26.8 | 19.1 | 106 | 20.7 | 80 |
| 39 | 1% | 3% | — | — | — | 180° C. | 30 | 4% | 0.5% | 0.15% | — | 25.6 | 19.7 | 67 | 20.6 | 94 |
| 40 | 1% | 3% | — | — | — | 170° C. | 90 | 4% | 0.5% | 0.15% | 0.15% | 26.8 | 18.8 | 94 | 20.2 | 94 |

TABLE 4

(1 molEDA + 3.7 molAGE + 0.035% SR454) Examples 41-60 of Particulate Superabsorbent Polymer Composition including Internal Crosslinker including Internal Crosslinker 1 plus a second internal crosslinker 1.92 g of Internal Crosslinker 1 and 0.224 g of SR-454 were added to the solution as set forth in making the Particulate Superabsorbent Polymer Composition and the resulting particulate superabsorbent polymer was surface crosslinked and surface treated as set forth in Table 4 to form Examples 41-60 of the particulate superabsorbent polymer composition.

| | Pre-Treatment before SX | | | | SX step | | Post-treatment after SX | | | | Properties | | | | |
|---|---|---|---|---|---|---|---|---|---|---|---|---|---|---|---|
| No. | EC | Water | Silica | Al-lactate | Al-Sulfate | Temperature | Time min | Water | Silica | Al-lactate | Al-Sulfate | CRC | AUL (0.9 psi) | GBP | AAP (0.7 psi) | SFC |
| 41 | 1% | 3% | — | 0.3% | — | 180° C. | 30 | — | — | — | — | 27.8 | 23.1 | 11 | 24.0 | 46 |
| 42 | 1% | 3% | — | 0.3% | — | 170° C. | 90 | — | — | — | — | 28.0 | 23.1 | 12 | 24.2 | 55 |
| 43 | 1% | 3% | — | — | 0.3% | 180° C. | 30 | — | — | — | — | 28.1 | 23.4 | 26 | 23.8 | 63 |
| 44 | 1% | 3% | — | — | 0.3% | 170° C. | 90 | — | — | — | — | 27.3 | 23.3 | 52 | 24.0 | 67 |
| 45 | 1% | 3% | 0.5% | — | — | 180° C. | 30 | — | — | — | — | 27.7 | 20.6 | 115 | 21.8 | 153 |
| 46 | 1% | 3% | 0.5% | — | — | 170° C. | 90 | — | — | — | — | 27.4 | 20.6 | 57 | 22.0 | 151 |
| 47 | 1% | 3% | 0.5% | 0.3% | — | 180° C. | 30 | — | — | — | — | 27.8 | 21.2 | 50 | 21.2 | |
| 48 | 1% | 3% | 0.5% | 0.3% | — | 170° C. | 90 | — | — | — | — | 27.6 | 20.8 | 47 | 21.7 | |
| 49 | 1% | 3% | 0.5% | —% | 0.3% | 180° C. | 30 | — | — | — | — | 26.5 | 20.9 | 47 | 21.8 | |
| 50 | 1% | 3% | 0.5% | —% | 0.3% | 170° C. | 90 | — | — | — | — | 27.1 | 20.3 | 34 | 22.4 | |
| 51 | 1% | 3% | 0.5% | 0.15% | 0.15% | 180° C. | 30 | — | — | — | — | 27.8 | 20.0 | 87 | 21.3 | |
| 52 | 1% | 3% | 0.5% | 0.15% | 0.15% | 170° C. | 90 | — | — | — | — | 27.9 | 21.1 | 74 | 21.9 | |
| 53 | 1% | 3% | — | — | — | 180° C. | 30 | —% | 0.5% | — | — | 27.4 | 23.3 | 11 | 25.0 | 29 |
| 54 | 1% | 3% | — | — | — | 170° C. | 90 | —% | 0.5% | — | — | 27.3 | 23.4 | 17 | 24.8 | 45 |
| 55 | 1% | 3% | — | — | — | 180° C. | 30 | 4% | 0.5% | 0.3% | — | 27.1 | 19.7 | 56 | 21.4 | |
| 56 | 1% | 3% | — | — | — | 170° C. | 90 | 4% | 0.5% | 0.3% | — | 26.6 | 19.5 | 54 | 21.6 | |
| 57 | 1% | 3% | — | — | — | 180° C. | 30 | 4% | 0.5% | — | 0.3% | 26.0 | 19.6 | 44 | 20.3 | |
| 58 | 1% | 3% | — | — | — | 170° C. | 90 | 4% | 0.5% | — | 0.3% | 26.2 | 19.8 | 67 | 21.7 | |
| 59 | 1% | 3% | — | — | — | 180° C. | 30 | 4% | 0.5% | 0.15% | 0.15% | 26.8 | 19.9 | 53 | 21.5 | |
| 60 | 1% | 3% | — | — | — | 170° C. | 90 | 4% | 0.5% | 0.15% | 0.15% | 26.7 | 20.3 | 51 | 21.7 | |

TABLE 5

(1 molEDA + 3.7 molAGE + 0.035% SR454) Examples 61-80 of Particulate Superabsorbent Polymer Composition including Internal Crosslinker including Internal Crosslinker 1 plus a second internal crosslinker 1.92 g of Internal Crosslinker 2 and 0.224 g of SR-454 were added to the solution as set forth in making the Particulate Superabsorbent Polymer Composition and the resulting particulate superabsorbent polymer was surface crosslinked and surface treated as set forth in Table 5 to form Examples 61-80 of the particulate superabsorbent polymer composition.

| | Pre-Treatment before SX | | | | SX step | | Post-treatment after SX | | | | Properties | | | | |
|---|---|---|---|---|---|---|---|---|---|---|---|---|---|---|---|
| No. | EC | Water | Silica | Al-lactate | Al-Sulfate | Temperature | Time min | Water | Silica | Al-lactate | Al-Sulfate | CRC | AUL (0.9 psi) | GBP | AAP (0.7 psi) | SFC |
| 61 | 1% | 3% | — | 0.3% | — | 180° C. | 30 | — | — | — | — | 27.6 | 22.5 | 9 | 24.0 | 47 |
| 62 | 1% | 3% | — | 0.3% | — | 170° C. | 90 | — | — | — | — | 27.7 | 22.9 | 13 | 24.1 | 46 |
| 63 | 1% | 3% | — | — | 0.3% | 180° C. | 30 | — | — | — | — | 27.1 | 22.2 | 32 | 23.1 | 51 |
| 64 | 1% | 3% | — | — | 0.3% | 170° C. | 90 | — | — | — | — | 26.7 | 22.5 | 22 | 23.5 | 49 |
| 65 | 1% | 3% | 0.5% | — | — | 180° C. | 30 | — | — | — | — | 27.2 | 19.1 | 101 | 21.6 | 65 |
| 66 | 1% | 3% | 0.5% | — | — | 170° C. | 90 | — | — | — | — | 27.6 | 19.9 | 92 | 21.8 | 70 |
| 67 | 1% | 3% | 0.5% | 0.3% | — | 180° C. | 30 | — | — | — | — | 27.0 | 19.1 | 97 | 20.7 | 101 |
| 68 | 1% | 3% | 0.5% | 0.3% | — | 170° C. | 90 | — | — | — | — | 27.2 | 19.3 | 123 | 21.5 | 107 |
| 69 | 1% | 3% | 0.5% | — | 0.3% | 180° C. | 30 | — | — | — | — | 27.2 | 19.2 | 110 | 21.6 | 110 |
| 70 | 1% | 3% | 0.5% | — | 0.3% | 170° C. | 90 | — | — | — | — | 26.9 | 19.8 | 121 | 21.4 | 97 |
| 71 | 1% | 3% | 0.5% | 0.15% | 0.15% | 180° C. | 30 | — | — | — | — | 27.1 | 20.7 | 34 | 20.9 | 69 |
| 72 | 1% | 3% | 0.5% | 0.15% | 0.15% | 170° C. | 90 | — | — | — | — | 26.8 | 23.4 | 94 | 22.0 | 134 |
| 73 | 1% | 3% | — | — | — | 180° C. | 30 | — | 0.5% | — | — | 26.9 | 23.2 | 15 | 24.6 | 60 |
| 74 | 1% | 3% | — | — | — | 170° C. | 90 | — | 0.5% | — | — | 27.8 | 23.3 | 12 | 24.6 | 50 |
| 75 | 1% | 3% | — | — | — | 180° C. | 30 | 4% | 0.5% | 0.3% | — | 25.7 | 19.2 | 86 | 21.1 | 95 |
| 76 | 1% | 3% | — | — | — | 170° C. | 90 | 4% | 0.5% | 0.3% | — | 26.7 | 19.0 | 86 | 21.0 | 73 |
| 77 | 1% | 3% | — | — | — | 180° C. | 30 | 4% | 0.5% | — | 0.3% | 25.4 | 19.9 | 99 | 21.4 | 105 |
| 78 | 1% | 3% | — | — | — | 170° C. | 90 | 4% | 0.5% | — | 0.3% | 26.4 | 20.0 | 121 | 20.9 | 85 |
| 79 | 1% | 3% | — | — | — | 180° C. | 30 | 4% | 0.5% | 0.15% | 0.15% | 25.7 | 19.8 | 102 | 21.0 | 78 |
| 80 | 1% | 3% | — | — | — | 170° C. | 90 | 4% | 0.5% | 0.15% | 0.15% | 26.5 | 19.9 | 86 | 21.0 | 89 |

As shown in Examples 1-80 in the foregoing tables, that superabsorbent polymers made with internal crosslinker composition comprising the reaction product of amines and glycidyl compounds and having low residual amounts of glycidyl compounds in the internal crosslinker composition result in superabsorbent polymer compositions having desirous performance properties.

Notwithstanding that the numerical ranges and parameters setting forth the broad scope of the invention are approximations, the numerical values set forth in the specific examples are reported as precisely as possible. Other than in the operating examples, or where otherwise indicated, all numbers expressing quantities of ingredients, reaction conditions, and so forth used in the specification and claims are to be understood as being modified in all instances by the term "about". Any numerical value, however, inherently contain certain errors necessarily resulting from the standard deviation found in their respective testing measurements.

What is claimed is:

1. A process to make a particulate superabsorbent polymer composition having increased permeability comprising the steps of
   a) preparing a neutralized monomer solution comprising a polymerizable monomer selected from unsaturated acid groups-containing monomers, ethylenically unsaturated carboxylic acid anhydride, salts, or derivatives thereof and a caustic agent selection from an alkali agent, wherein the polymerizable monomer is neutralized to from about 50 mol % to about 85 mol %;
   b) forming a crosslinker monomer mixture by adding an internal crosslinker composition to the neutralized monomer solution wherein the internal crosslinker composition is the reaction product of amines and glycidyl compounds selected from,
      (i) saturated amines and/or saturated polyamines with ethylenically unsaturated glycidyl and/or ethylenically unsaturated polyglycidyl compounds, or
      (ii) ethylenically unsaturated amines and/or ethylenically unsaturated polyamines with saturated glycidyl compounds and/or saturated polyglycidyl compounds, or
      (iii) ethylenically unsaturated amines and/or ethylenically unsaturated polyamines with ethylenically unsaturated glycidyl compounds and/or ethylenically unsaturated polyglycidyl compounds;
   wherein the amount of the amines and glycidyl compounds includes a stoichiometric excess of amines/unreacted amino functions wherein the amount of the glycidyl groups is from 75% to 98% of the molar amount of the NH-functions, and the internal crosslinker composition has a residual amount of glycidyl compounds of less than about 500 ppm based on the mass of the internal crosslinker composition as determined by the Glycidyl Compound in Amine-Glycidyl Compound Reaction Products Test set forth herein;
   c) polymerizing the crosslinker monomer mixture to make a superabsorbent polymer wherein components a) and b) are polymerized;
   d) granulating the superabsorbent polymer of step c) to form superabsorbent polymer particles having a surface and wherein at least about 40 wt % of the superabsorbent polymer particles have a size of from about 150 μm to about 850 μms; and
   e) surface treating the particulate superabsorbent polymer with from about 0.01 to about 5 wt % based on a dry particulate superabsorbent polymer composition weight of surface crosslinking agent applied to the particle surface;
   wherein the particulate superabsorbent polymer composition has a Centrifuge Retention Capacity of from about 20 g/g to about 40 g/g as determined by the Centrifuge Retention Capacity Test set forth herein, and a Gel Bed Permeability of at least about 5 Darcy or more as determined by the Free-Swell Gel Bed Permeability Test set forth herein.

2. The process according to claim 1 further comprising the steps of f) heat treating the superabsorbent polymer particles of step e) at a temperature of from about 150° C. to about 250° C. for about 20 to about 120 minutes to form a particulate superabsorbent polymer composition.

3. The process according to claim 2 further comprising a step of g) adding from about 0.01 to about 5 wt % based on the particulate superabsorbent polymer composition weight of an insoluble, inorganic powder during step e) or subsequent to step f); wherein the particulate superabsorbent polymer composition has a Gel Bed Permeability of from about 30 to about 150 Darcy as determined by the Free-Swell Gel Bed Permeability Test set forth herein.

4. The process according to claim 2 further comprising a step of h) adding from about 0.01 to about 5 wt % based on the particulate superabsorbent polymer composition weight of a multivalent metal salt during step e) or subsequent step f).

5. The process according to claim 4 wherein the multivalent metal salt comprises aluminum sulfate and the particulate superabsorbent polymer composition has a Centrifuge Retention Capacity of from 20 g/g to 40 g/g as determined by the Centrifuge Retention Capacity Test set forth herein, and a Gel Bed Permeability value of from about 20 Darcy to about 200 Darcy, as determined by the Free-Swell Gel Bed Permeability Test set forth herein, an Absorbency Under Load at 0.9 psi (AUL(0.9 psi)) of from 12 g/g to 40 g/g as determined by the Absorbency Under Load(0.9 psi) Test set forth herein; or having an Absorbency At Pressure at 0.7 psi (AAP(0.7 psi)) of from 15 g/g to 40 g/g as determined by the Absorbency At Pressure at 0.7 psi Test as set forth herein; or having an Saline Flow Conductivity of from $20 \times 10^{-7} * cm^3 * s * g^{-1}$ to $200 \times 10^{-7} * cm^3 * s * g^{-1}$ as determined by the Saline Flow Conductivity (SFC) Test as set forth herein.

6. The process according to claim 2 wherein the amount of the glycidyl groups is from 85% to 98% of the molar amount of the NH-functions and the particulate superabsorbent polymer composition has a internal crosslinker composition which has a residual glycidyl of less than about 100 ppm as determined by the Glycidyl Compound in Amine-Glycidyl Compound Reaction Products Test set forth herein.

7. The process according to claim 1 wherein the ethylenically unsaturated glycidyl compounds and/or ethylenically unsaturated polyglycidyl compounds are selected from ethylene glycol monoglycidyl ether and the related $C_1$-$C_6$-alkyl ethers or esters thereof; glycidol, ethylene oxide, propylene oxide, (meth)allyl glycidyl ethers, polyethylene glycol monoglycidyl ethers and the related $C_1$-$C_6$-alkyl ethers or esters thereof; vinyl glycidyl ethers, glycidyl(meth)acrylates, glycidyl(meth)allyl ethers, or 1-halogen-2,3-epoxypropane; ethylene glycol or polyglycol diglycidyl ethers; glycerol, trimethylolpropane, or pentaerythritol triglycidyl ethers; polyglycerol polyglycidyl ethers, sorbitol polyglycidyl ethers, or the mixtures thereof.

8. The process according to claim 1 wherein the ethylenically unsaturated glycidyl and/or ethylenically unsaturated polyglycidyl compounds comprise glycidyl compounds that comprise polyethylene glycol chains having from about 0.3 about 0.4 mol of propylene oxide per mol of internal crosslinker composition.

9. The process according to claim 1 wherein the ethylenically unsaturated glycidyl and/or ethylenically unsaturated polyglycidyl compounds are selected from (meth)allyl glycidyl ethers or glycidyl (meth)acrylate.

10. The process according to claim 1 wherein the saturated amines and/or saturated polyamines or ethylenically unsaturated amines and/or ethylenically unsaturated polyamines are selected from (mono, di and poly)aminoalkanes, (mono, di and poly)aminopolyethers, allylamine, alkyl(meth)allylamines, e.g., methyl allylamine, methyl methallylamine, ethyl methallylamine, and ethyl allylamine; methyl-, ethyl-, propyl- and butylamine, diallylamine, dimethallylamine, aniline, ethylenediamine, diethylenetriamine, hexamethylenediamine, trimethylhexamethylenediamine, neopentane diamine, 1,2-propylenediamine, 4,7-dioxadecane-1,10-diamine, 4,9-dioxadodecane-1,12-diamine, polyether diamines, polyalkylene glycol diamines, 3-amino-1-methylaminopropane, bis(3-aminopropyl)methylamine, isophorone diamine, 4,4'-diaminodicyclohexylmethane, 1-(2-aminoethyl)piperazine, o-, m-, or p-phenylenediamine, 4,4'-diaminodiphenylmethane, 1,4-diaminoanthraquinone, 2,4,6-triamino-1,3,5-triazine, aminopyridine, glucosamine, and mixtures thereof.

11. The process according to claim 1 wherein the saturated amines and/or saturated polyamines or ethylenically unsaturated amines and/or ethylenically unsaturated polyamines are selected from ethylene diamine, diallylamine, diethylene triamine, or hexamethylenediamine.

12. The process according to claim 1 further comprises from about 0.01 to about 1 wt % based on the monomer of a second internal crosslinker composition.

13. The process according to claim 12 wherein the second internal crosslinker composition is selected from methylenebisacrylamide or -methacrylamide or ethylenebisacrylamide; esters of unsaturated mono- or polycarboxylic acids of polyols including diacrylates or triacrylates, butanediol- or ethylene glycol diacrylate or -methacrylate; trimethylolpropane triacrylate, and their alkoxylates; allyl compounds including allyl (meth)acrylate, triallyl cyanurate, maleic acid diallyl ester, polyallyl ester, tetraallyloxyethane, di- and triallylamine, tetrallylethylenediamine, allyl esters of phosphoric acid or phosphorous acid.

14. The process according to claim 1 wherein the unsaturated, acid groups-containing monomers are selected from acrylic acid, methacrylic acid, vinyl acetic acid, vinyl sulfonic acid, methallyl sulfonic acid, and 2-acrylamido-2-methylpropane sulfonic acid.

15. The process according to claim 1 which additionally comprises from 0 to about 40%-wt, relative to the acid monomers, of comonomers selected from the group consisting of (meth)acrylamide, (meth)acrylonitrile, vinyl pyrrolidone, hydroxyethyl acrylate, and vinyl acetamide.

16. The process according to claim 2 wherein the surface crosslinking agent is ethylene carbonate.

17. The process according to claim 2 further comprising the step of surface treating the superabsorbent polymer particles with from about 0.001 to about 0.5 wt % based on the particulate superabsorbent polymer composition of a thermoplastic polymer.

18. The process according to claim 1 further comprising the step of alkoxylating the internal crosslinker composition with ethylene oxide or propylene oxide.

19. A particulate superabsorbent polymer composition having increased permeability wherein the particulate superabsorbent polymer composition comprises
  a) a polymerizable monomer wherein the polymerizable monomer is selected from unsaturated acid groups-containing monomers, ethylenically unsaturated carboxylic acid anhydride, salts, or derivatives thereof;
  b) an internal crosslinker composition that is the reaction product selected from
    (i) saturated amines and/or saturated polyamines with ethylenically unsaturated glycidyl compounds and/or ethylenically unsaturated polyglycidyl compounds, or
    (ii) ethylenically unsaturated amines and/or ethylenically unsaturated polyamines with saturated glycidyl compounds and/or saturated polyglycidyl compounds, or
    (iii) ethylenically unsaturated amines and/or ethylenically unsaturated polyamines with ethylenically unsaturated glycidyl compounds and/or ethylenically unsaturated polyglycidyl compounds;
  wherein components a) and b) are polymerized and granulated to form particulate superabsorbent polymer which has a particle surface, wherein at least about 40 wt % of the particulate superabsorbent polymer has a particle size from about 300 μm to about 600 μm;
  c) from about 0.01 to about 5 wt % based on a dry particulate superabsorbent polymer composition weight of surface crosslinking agent applied to the particle surface;
  wherein the amount of the amines and glycidyl compounds includes a stoichiometric excess of amines wherein the amount of the glycidyl groups is from 75% to 98% of the molar amount of the NH-functions, and the internal crosslinker composition has a residual glycidyl of less than about 500 ppm based on the mass of the internal crosslinker composition as determined by the Glycidyl Compound in Amine-Glycidyl Compound Reaction Products Test set forth herein; and
  wherein the particulate superabsorbent polymer composition has a Centrifuge Retention Capacity of from about 20 g/g to about 40 g/g as determined by the Centrifuge Retention Capacity Test set forth herein, and a Gel Bed Permeability of at least about 5 Darcy or more as determined by the Free-Swell Gel Bed Permeability Test set forth herein.

20. The particulate superabsorbent polymer composition of claim 19 wherein the amount of the glycidyl groups is from 85% to 98% of the molar amount of the NH-functions and the internal crosslinker composition has a residual glycidyl compounds of less than about 100 ppm as determined by the Glycidyl Compound in Amine-Glycidyl Compound Reaction Products Test set forth herein.

21. The particulate superabsorbent polymer composition of claim 19 further comprising d) from about 0.01 to about 5 wt % based on the dry particulate superabsorbent polymer composition weight of an insoluble, inorganic powder; wherein the particulate superabsorbent polymer composition has a Gel Bed Permeability of from about 10 to about 200 Darcy as determined by the Free-Swell Gel Bed Permeability Test set forth herein.

22. The particulate superabsorbent polymer composition of claim 19 further comprising e) from about 0.01 to about 5 wt % based on the dry particulate superabsorbent polymer composition weight of a multivalent metal salt.

23. The particulate superabsorbent polymer composition of claim 19 wherein the ethylenically unsaturated glycidyl compounds and/or ethylenically unsaturated polyglycidyl compounds are selected from ethylene glycol monoglycidyl ether and the related $C_1$-$C_6$-alkyl ethers or esters thereof; glycidol, ethylene oxide, propylene oxide, (meth)allyl glycidyl ethers, polyethylene glycol monoglycidyl ethers and the related $C_1$-$C_6$-alkyl ethers or esters thereof vinyl glycidyl ethers, glycidyl(meth)acrylates, glycidyl(meth)allyl ethers, or 1-halogen-2,3-epoxypropane; ethylene glycol or polyglycol diglycidyl ethers; glycerol, trimethylolpropane, or pentaerythritol triglycidyl ethers; polyglycerol polyglycidyl ethers, sorbitol polyglycidyl ethers, or their mixtures thereof.

24. The particulate superabsorbent polymer composition of claim 19 wherein the ethylenically unsaturated glycidyl compounds and/or ethylenically unsaturated polyglycidyl compounds comprise glycidyl compounds that comprise polyethylene glycol chains having from about 0.3 about 0.4 mol of propylene oxide per mol of internal crosslinker composition.

25. The particulate superabsorbent polymer composition of claim 19 wherein the ethylenically unsaturated glycidyl compounds and/or ethylenically unsaturated polyglycidyl compounds are selected from (meth)allyl glycidyl ethers or glycidyl (meth)acrylate.

26. The particulate superabsorbent polymer composition of claim 19 wherein the saturated amines and/or saturated polyamines or ethylenically unsaturated amines and/or ethylenically unsaturated polyamines are selected from (mono, di and poly)aminoalkanes, (mono, di and poly)aminopolyethers, allylamine, alkyl(meth)allylamines, e.g., methyl allylamine, methyl methallylamine, ethyl methallylamine, and ethyl allylamine; methyl-, ethyl-, propyl- and butylamine, diallylamine, dimethallylamine, aniline, ethylenediamine, diethylenetriamine, hexamethylenediamine, trimethylhexamethylenediamine, neopentane diamine, 1,2-propylenediamine, 4,7-dioxadecane-1,10-diamine, 4,9-dioxadodecane-1,12-diamine, polyether diamines, polyalkylene glycol diamines, 3-amino-1-methylaminopropane, bis(3-aminopropyl)methylamine, isophorone diamine, 4,4'-diaminodicyclohexylmethane, 1-(2-aminoethyl)piperazine, o-, m-, or p-phenylenediamine, 4,4'-diaminodiphenylmethane, 1,4-diaminoanthraquinone, 2,4,6-triamino-1,3,5-triazine, aminopyridine, glucosamine, and mixtures thereof.

27. The particulate superabsorbent polymer composition of claim 19 wherein the saturated amines and/or saturated polyamines or ethylenically unsaturated amines and/or ethylenically unsaturated polyamines are selected from ethylene diamine, diallylamine, diethylene triamine, or hexamethylenediamine.

28. The particulate superabsorbent polymer composition of claim 19 further comprising from about 0.01 to about 1 wt % based on the polymerizable monomer of a second internal crosslinker composition.

29. The particulate superabsorbent polymer composition of claim 28 wherein the second internal crosslinker composition is selected from methylenebisacrylamide or -methacrylamide or ethylenebisacrylamide; esters of unsaturated mono- or polycarboxylic acids of polyols including diacrylates or triacrylates, butanediol- or ethylene glycol diacrylate or -methacrylate; trimethylolpropane triacrylate, and their alkoxylates; allyl compounds including allyl (meth)acrylate, triallyl cyanurate, maleic acid diallyl ester, polyallyl ester, tetraallyloxyethane, di- and triallylamine, tetrallylethylenediamine, allyl esters of phosphoric acid or phosphorous acid.

30. The particulate superabsorbent polymer composition of claim 19 wherein the unsaturated, acid groups-containing monomers are selected from acrylic acid, methacrylic acid, vinyl acetic acid, vinyl sulfonic acid, methallyl sulfonic acid, and 2-acrylamido-2-methylpropane sulfonic acid.

31. The particulate superabsorbent polymer composition of claim 19 further comprising from 0 to about 40 wt %, relative to the polymerizable monomers of comonomers selected from the group consisting of (meth)acrylamide, (meth)acrylonitrile, vinyl pyrrolidone, hydroxyethyl acrylate, and vinyl acetamide.

32. The particulate superabsorbent polymer composition of claim 19 wherein the surface crosslinking agent is ethylene carbonate.

33. The particulate superabsorbent polymer composition of claim 19 further comprising from about 0.001 to about 0.5 wt % based on the dry particulate superabsorbent polymer composition weight of a thermoplastic polymer.

34. The particulate superabsorbent polymer composition of claim 19 wherein the surface crosslinked superabsorbent polymer particles have an Absorbency Under Load at about 0.9 psi (AUL(0.9 psi)) from about 12 g/g to about 30 g/g as determined by the Absorbency Under Load(0.9 psi) Test set forth herein.

35. An absorbent article comprising the particulate superabsorbent polymer composition of claim 19.

36. The particulate superabsorbent polymer composition of claim 19 wherein the internal crosslinker composition with ethylene oxide or propylene oxide.

37. The process according to claim 1 further comprising the step of g) adding from about 0.01 to about 5 wt % based on the dry particulate superabsorbent polymer composition weight of an insoluble, inorganic powder to the surface of the superabsorbent polymer particle; wherein the particulate superabsorbent polymer composition has a Gel Bed Permeability of from about 10 to about 200 Darcy as determined by the Free-Swell Gel Bed Permeability Test set forth herein.

38. The process according to claim 1 further comprising the step of h) adding from about 0.01 to about 5 wt % based on the dry particulate superabsorbent polymer composition weight of a multivalent metal salt.

\* \* \* \* \*